US011839511B2

(12) United States Patent
Caluser et al.

(10) Patent No.: US 11,839,511 B2
(45) Date of Patent: Dec. 12, 2023

(54) SYSTEM AND METHOD FOR TRACKING COMPLETENESS OF CO-REGISTERED MEDICAL IMAGE DATA

(71) Applicant: Metritrack, Inc., Hillside, IL (US)

(72) Inventors: Calin Caluser, Glen Ellyn, IL (US); Guang Yang, Hoffman Estates, IL (US)

(73) Assignee: Metritrack, Inc., Hillside, IL (US)

( * ) Notice: Subject to any disclaimer, the term of this patent is extended or adjusted under 35 U.S.C. 154(b) by 344 days.

(21) Appl. No.: 16/948,212

(22) Filed: Sep. 9, 2020

(65) Prior Publication Data

US 2021/0068782 A1 Mar. 11, 2021

Related U.S. Application Data

(60) Provisional application No. 62/973,007, filed on Sep. 10, 2019.

(51) Int. Cl.
*A61B 8/00* (2006.01)
*A61B 8/08* (2006.01)

(52) U.S. Cl.
CPC .......... *A61B 8/4245* (2013.01); *A61B 8/0841* (2013.01); *A61B 8/461* (2013.01);
(Continued)

(58) Field of Classification Search
CPC ..... A61B 8/4245; A61B 8/0841; A61B 8/461; A61B 8/58; A61B 2562/0223;
(Continued)

(56) References Cited

U.S. PATENT DOCUMENTS 6,709,387 B1    3/2004   Glukhovsky et al.
2005/0110881 A1   5/2005   Glukhovsky et al.
(Continued)

FOREIGN PATENT DOCUMENTS

WO    WO-2008071454 A2 *   6/2008  .......... A61B 5/7207

OTHER PUBLICATIONS

Potter et al., "Detecting meaning in RSVP at 13 ms per picture," Psychonomic Society, Inc. 2014, vol. 76, pp. 270-279, Published online: Dec. 28, 2013.
(Continued)

*Primary Examiner* — Colin T. Sakamoto
(74) *Attorney, Agent, or Firm* — Vedder Price P.C.

(57) ABSTRACT

An ultrasound image tracking completeness system includes an ultrasound imaging probe that acquires images during an examination, an imaging probe sensor coupled to the ultrasound imaging probe and that tracks a position and an orientation of the ultrasound imaging probe, and a display to display images acquired by the ultrasound imaging probe. The system also includes a processor programmed to calculate a probe speed threshold at which the ultrasound imaging probe may be moved while acquiring images during the examination, track the position and orientation of the ultrasound imaging probe during the examination by monitoring the imaging probe sensor, determine a movement speed of the ultrasound imaging probe during the examination, and if the movement speed of the ultrasound imaging probe exceeds the probe speed threshold, issue a warning to an operator.

7 Claims, 21 Drawing Sheets

(52) U.S. Cl.
CPC .............. *A61B 8/58* (2013.01); *A61B 8/0825* (2013.01); *A61B 2562/0223* (2013.01)

(58) Field of Classification Search
CPC ... A61B 8/0825; A61B 8/4254; A61B 8/4263; A61B 8/483; A61B 8/523; A61B 8/5238; A61B 8/5246; A61B 8/5253
See application file for complete search history.

(56) References Cited

U.S. PATENT DOCUMENTS

| | | |
|---|---|---|
| 2006/0100515 A1 | 5/2006 | Nakata |
| 2007/0078342 A1 | 4/2007 | Jago |
| 2009/0041323 A1 | 2/2009 | Lachaine et al. |
| 2013/0046175 A1* | 2/2013 | Sumi ..................... A61B 8/483 600/431 |
| 2015/0051489 A1 | 2/2015 | Caluser et al. |
| 2015/0213725 A1 | 7/2015 | Huntley et al. |
| 2016/0100821 A1 | 4/2016 | Eggers et al. |
| 2018/0028156 A1 | 2/2018 | Matsunaga et al. |
| 2018/0132722 A1* | 5/2018 | Eggers ................ A61B 5/0033 |
| 2020/0367860 A1* | 11/2020 | Rouet .................. A61B 8/4254 |
| 2022/0148199 A1* | 5/2022 | Bauer ................... A61B 8/483 |

OTHER PUBLICATIONS

EPO Communication Extended Search Report filed in European Application No. 20863152.3; dated Aug. 16, 2023; 9 pages.

\* cited by examiner

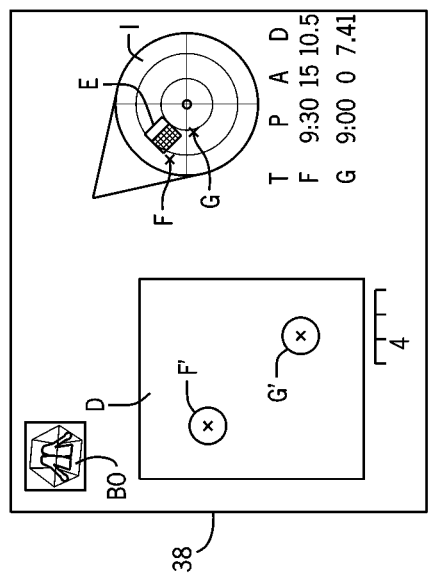
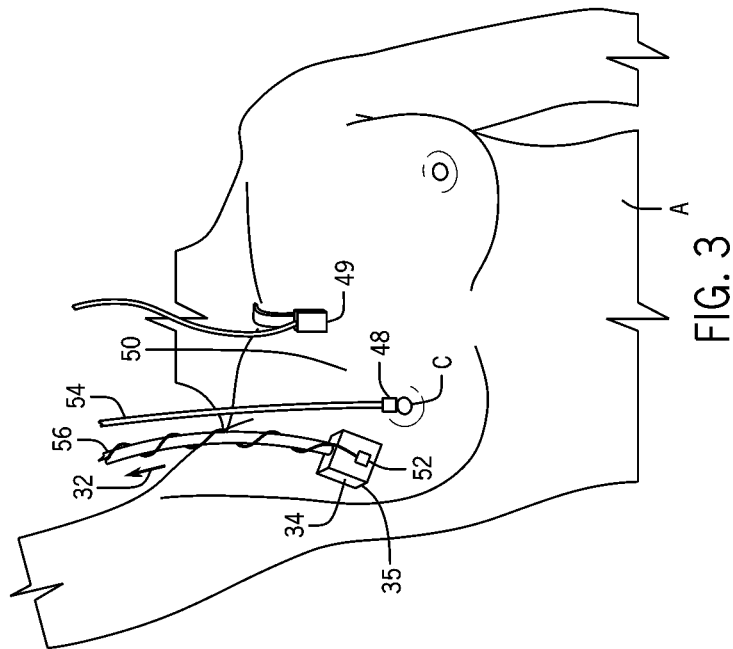
FIG. 4
FIG. 3

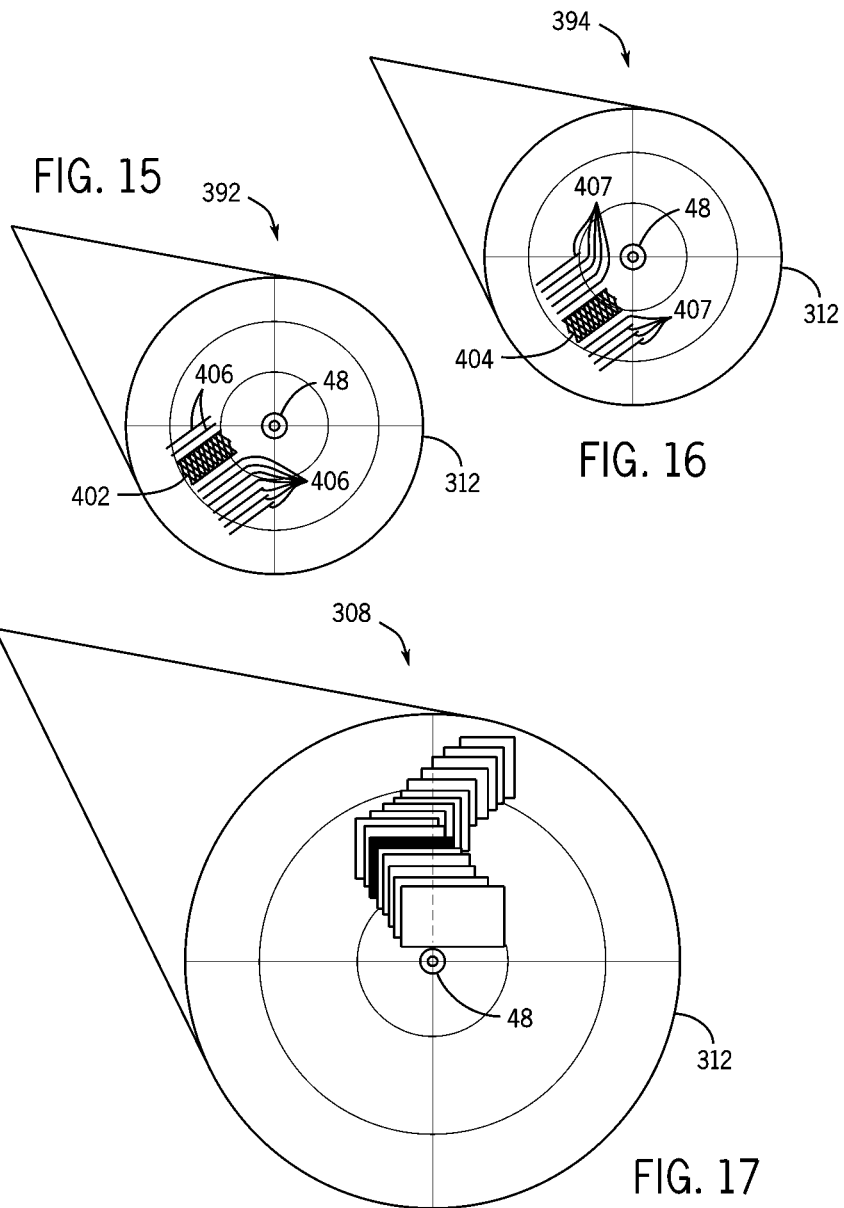

SYSTEM AND METHOD FOR TRACKING COMPLETENESS OF CO-REGISTERED MEDICAL IMAGE DATA

CROSS-REFERENCE TO RELATED APPLICATIONS

This application is a nonprovisional of and claims the benefit of U.S. Patent Application Ser. No. 62/973,007, filed Sep. 10, 2019, the disclosure of which is incorporated herein by reference in its entirety.

GOVERNMENT RIGHTS IN THE INVENTION

This invention was made with Government support under contract number R43CA235912 awarded by the National Institutes of Health. The Government has certain rights in the invention.

BACKGROUND OF THE INVENTION

Embodiments of the invention relate generally to medical imaging and, more particularly, to a system and method for system for analyzing image data acquired from an imaging modality, generating a surface contour of a region of interest (ROI), and determining the completeness of the acquired image data within the ROI.

Ultrasound imaging systems transmit sound waves of very high frequency (e.g., 1 MHz to 20 MHz) into the patient's body and the echoes scattered from structures in the patient's body are processed to create and display images and information related to these structures. Ultrasound is an important imaging modality for medical diagnostic purposes and as a guidance tool for diagnostic or screening purposes and for therapeutic procedures, such as, for example soft tissue needle biopsy, tumor ablation, and the like. A diagnostic ultrasound examination is performed to address a specific medical concern and provide additional evaluation to reach the diagnosis. For example, in breast ultrasound, a diagnostic examination can be performed to evaluate a palpable lump or focal pain or evaluate a lesion detected with other modality like mammography or MRI. A screening examination, on the other hand, is usually performed to detect occult pathology in a group of people which carry a certain risk for a disease or group of diseases, and can be used to increase the detection rate for small cancers, such as in the case of women with dense mammograms. In addition, handheld ultrasound guidance can be used for the guidance of medical instruments or procedures, like needle biopsies, surgery, treatment delivery and more. Ultrasound can be used over the entire human body and has certain advantages over other modalities, including, among others: the ability to locate and characterize medical problems, lower cost compared to modalities such as MRI and CT, real-time operation and image display, and the lack of ionizing radiation with the known associated health risks.

2D free hand ultrasound imaging, the most common technique used today, represents a slice through the region of interest. During a breast ultrasound procedure, for example, the radiologist, technician, or other medical professional (the "operator") places an ultrasound transducer over a region of interest of the breast and is then able to view a real-time ultrasound image that is output on a display. In addition to the ultrasound image, the display may also include relevant text and/or graphical information for simultaneous viewing by the operator. The operator can freeze a displayed 2D image with medical findings of interest, and the corresponding image can be printed on a printer or stored in digital format.

Ultrasound procedures are highly dependent on the device user's experience and training. The vast majority of ultrasound examinations are conducted free hand, with the operator holding the ultrasound transducer in one hand and use the other hand to operate the ultrasound machine controls. The operator pauses movement of the ultrasound probe upon viewing a possible lesion, tumor, or other specious finding in a displayed image and will then manually mark the location of the suspicious finding in the image, often by entering alpha numerical characters or graphical signs.

Position recording of suspicious findings is important, especially for small targets and/or multiple targets identified in an image or series of acquired images. The smaller the tumor is before treatment, the higher the probability of long-term patient survival or cure. However, small tumors are difficult to find in a patient's body and difficult to differentiate from other structures or artifacts in the same region. Many times, a suspicious small finding can coexist in the same region with multiple benign findings (cysts, solid benign nodules, etc.) with similar appearance, which may create confusion during a follow-up examination and may lead to missing the suspicious lesion. As imaging diagnostic devices provide ever greater detail and sub-millimeter resolution, accurate position registration and mapping of lesions is becoming increasingly important in order to take advantage of the increased capabilities.

The American College of Radiology (ACR) recommends that all ultrasound images be properly labeled. For example, for breast ultrasound images, the findings position, in hourly format, distance from Nipple C and ultrasound probe position and orientation should be displayed with the ultrasound images. Currently, ultrasound findings are manually labeled by the operator by manually typing or selecting a graphical sign for the current position and orientation of the ultrasound probe and the approximate position of a suspicious lesion in the organ or part of the body, which is time consuming and prone to errors.

Because of the importance of properly locating targets in an acquired ultrasound image, it is desirable to obtain the instant recording of target coordinates seen in the ultrasound image in relation to the anatomical reference (for example, a nipple) and the simultaneous recording of the ultrasound probe position. Although ultrasound guidance systems and devices do exist, known systems do not offer a practical and accurate solution to mapping targets in 2D or 3D images with real-time correction for movement of the patient's body between images and motion of deformable tissue between images.

In addition to the accurate mapping of lesions found in the body, it is also important to acquire image data for the entire tissue volume within the region of interest in order to ensure a high-quality examination and to avoid missing lesions. However, since most ultrasound procedures are manually performed with handheld transducers, the completeness of the scan may be negatively affected by the skill level of the operator or by simple human error.

To acquire image data for an entire breast volume, the operator usually follows a scanning protocol, wherein the scanning is performed in parallel rows, in the transverse or longitudinal direction relative to the patient's body axes, or radial and anti-radial direction relative to the nipple. The individual ultrasound images acquired from the scan represent a 2D plane segments with x and y coordinates and known resolution parameters. Each ultrasound image has a certain orientation and position in space and the volume of interest to be scanned. The ultrasound images are obtained with the handheld transducer and ultrasound machine in sequence at a known frequency, while the transducer is moved over the patient's skin. The transducer's speed while translated and its rotation during scanning, leads to obtaining a sequence of ultrasound images which are spaced in the volume of interest. While the resolution in each 2D ultrasound image remains constant or can be controlled by the operator using the ultrasound machine controls, the spatial resolution in the Z-direction is dependent on the speed of manual translation and rotation of the transducer while scanning. A certain fixed or range of acceptable spatial resolution values between the neighboring ultrasound images must be maintained in order to prevent missing small lesions or to reconstruct 3D images of sufficient resolution in all planes. If the operator fails to maintain the correct transducer speed or orientation during imaging, or if the operator fails to properly follow a given imaging protocol, image data for the complete region of interest may not be acquired.

In addition to the physical spacing between images, to prevent missing segments of space of a minimum size that can contain a lesion or target of interest in the acquired images, there is a minimum amount of time needed to present a selected amount of space to an interpreter to detect a small target. Both conditions described above depend on the speed the ultrasound probe is moved over the skin. Detecting a lesion in sequentially presented images, like a movie, is a complex process. The lower the amount of time an image is presented to a viewer, the less likely it is to detect a feature in the image. For example, the feature detection in images dropped by 50% when the display, or dwell time per image, dropped from 80 ms to 20 ms, (Mary C. Potter et al, Detecting meaning in RSVP at 13 ms per picture, Atten Percept Psychophys (2014) 76:270-279)). The detection of small lesions in ultrasound images is difficult due to the low contrast resolution, heterogeneous variable background, and image artifacts which interfere with the interpretation. Therefore, in addition to the required minimum distance between images in the Z direction needed to avoid missing a small target with a minimum size, there is the need to show the amount of space containing the minimum size of the target long enough to make a detection. For example, if ultrasound images are acquired at a high frame rate, such as 100 fps, and the probe travels at 60 mm/s, the space between images in the Z direction is 0.6 mm, and a 1 mm target will be included in at least one image. However, the amount of time the target will be displayed is 17 to 34 ms if the target is included in 1 or 2 images, respectively. This amount of display time would be associated with a high chance of missing the target. When the probe speed drops to 10 mm, the target will be displayed in multiple sequential images for 100 ms, and the detection of a 1 mm target is much more likely.

As a result, it would be desirable to have an apparatus and automated method of assessing the completeness of scanning in the region of interest during a handheld ultrasound procedure to assure the examination quality and prevent missing lesions.

It would also be desirable to measure and record the completeness of the surface scanning over the region of interest and also the spacing between the sequential or neighboring ultrasound probe positions and images during real-time scanning.

It would further be desirable to generate a display indicating a measurement of completeness of scanning for the region of interest and provide a means of guiding the operator to areas or volumes that were missed during the scanning procedure.

Further, it would be desirable to record inter-image spacing of the still, sequential multiple 2D or 3D images acquired during a particular examination so that the information would be available at a later time for interpretation and also detect, map, and record portions of the region of interest with suboptimal to allow the operator to rescan these regions and, therefore, prevent missing lesions.

Further, it would be desirable to display a small target in an image for a minimum amount of time to enable the detection of such target with a high probability.

BRIEF STATEMENT OF THE INVENTION

The invention is directed to a system and method for tracking completeness of co-registered medical image data.

In accordance with one aspect of the invention, an ultrasound image tracking completeness system includes an ultrasound imaging probe configured to acquire images during an examination, the images calibrated to the ultrasound imaging probe. The ultrasound image tracking completeness system also includes an imaging probe sensor coupled to the ultrasound imaging probe, the imaging probe sensor comprising a magnetic sensor configured to track a position and an orientation of the ultrasound imaging probe. The ultrasound image tracking completeness system further includes a display included on or separate from the ultrasound imaging probe and configured to display the images acquired by the ultrasound imaging probe and a processor programmed to calculate a probe speed threshold at which the ultrasound imaging probe may be moved while acquiring images during the examination, track the position and orientation of the ultrasound imaging probe during the examination by monitoring the imaging probe sensor, determine a movement speed of the ultrasound imaging probe during the examination, and if the movement speed of the ultrasound imaging probe exceeds the probe speed threshold, issue a warning to an operator.

In accordance with another aspect of the invention, a method for tracking image completeness includes identifying an orientation and a position of an ultrasound imaging probe of an ultrasound imaging system relative to the ultrasound imaging system during an examination and acquiring image data from a patient using the ultrasound imaging probe during the examination, the image data calibrated to the ultrasound imaging probe. The method also includes tracking a position and an orientation of the ultrasound imaging probe during the examination using a magnetic sensor coupled to the ultrasound imaging probe, reconstructing a first image of the patient from the image data that comprises a first plurality of pixels, and reconstructing a second image of the patient from the image data that comprises a second plurality of pixels. The method further includes calculating a probe speed of the ultrasound imaging probe based on the tracked position and orientation of the ultrasound imaging probe, determining whether the probe speed meets a probe speed threshold, displaying, on a display, at least one of the first and second images, and generating a warning to an operator if the probe speed fails to meet the probe speed threshold.

In accordance with yet another aspect of the invention, a tracking completeness system includes an ultrasound imaging probe configured to acquire a plurality of images during an examination, the plurality of images calibrated to the ultrasound imaging probe. The tracking completeness system also includes an imaging probe sensor coupled to the ultrasound imaging probe, the imaging probe sensor comprising a magnetic sensor configured to track a position and an orientation of the ultrasound imaging probe. The tracking completeness system further includes a display configured to display the plurality of images acquired by the ultrasound imaging probe and a processor programmed to set a maximum distance threshold, set a minimum time threshold, calculate a probe speed threshold based on the maximum distance threshold and the minimum time threshold, track the position and orientation of the ultrasound imaging probe during the examination by monitoring the imaging probe sensor, calculate a movement speed of the ultrasound imaging probe from the plurality of images acquired by the ultrasound imaging probe, determine whether the movement speed of the ultrasound imaging probe exceeds the probe speed threshold, and if the movement speed of the ultrasound imaging probe exceeds the probe speed threshold, provide a warning to an operator that the movement speed of the ultrasound imaging probe exceeds the probe speed threshold.

Various other features and advantages will be made apparent from the following detailed description and the drawings.

BRIEF DESCRIPTION OF THE DRAWINGS

The drawings illustrate embodiments presently contemplated for carrying out the invention.

In the drawings:

FIG. 3 is a schematic diagram illustrating the relative positioning of an anatomical reference sensor, optional sternum sensor, and ultrasound probe sensor of the TDMD of FIG. 1 during an exemplary breast ultrasound examination.

FIG. 4 illustrates an exemplary body diagram and ultrasound image frame displayed on the display of the imaging system of FIG. 1.

FIG. 15 is an exemplary chest wall surface map that includes an area of suboptimal image acquisition.

FIG. 16 is an exemplary breast surface map that includes an area of suboptimal image acquisition.

FIG. 17 illustrates an exemplary breast diagram showing an image frame location with suboptimal voxel spacing.

DETAILED DESCRIPTION

The operating environment of the various embodiments of the invention are described below with respect to a 2D ultrasound imaging system. However, it will be appreciated by those skilled in the art that the invention the concepts disclosed herein may be extended to 3D ultrasound imaging systems as well as images obtained with a different imaging modality or combination of imaging modalities, such as, for example, x-ray, CT or MRI. Images separately acquired using any of these modalities may be co-registered in space with positional registration to the same anatomical sensor(s) or marker(s) and displayed in a similar manner as described below for ultrasound images. Further, embodiments of the invention may be used for ultrasound breast cancer screening or diagnostic breast ultrasound exams. Additionally, the techniques disclosed herein may be extended to image data acquired from other regions in the body such as, for example, the eye, liver, abdomen, neck, and kidneys.

Additionally, the images from an image-producing handheld device different from an ultrasound probe, such as a handheld gamma camera, near infrared handheld probe, or the like, may be positionally calibrated to the probe in a similar way to the ultrasound probe image calibration described below. These types of handheld imaging devices may be positionally tracked in real time in reference to anatomical reference sensors using similar methods as those described below, with the position information for the associated images determined in real time and displayed in correlation with the images obtained with the tracking methods described below or over other body maps or images after position registration.

Accordingly, it is to be understood that the embodiments of the invention described herein are not limited in application to the details of arrangements of the components set forth in the following description. As will be appreciated by those skilled in the art, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Unless defined otherwise, all technical and scientific terms used herein have the same meaning as commonly understood by one of ordinary skill in the art to which this invention belongs. Moreover, the singular forms "a", "an", and "the" include plural references unless the context clearly dictates otherwise. Further, an "ultrasound frame" or "ultrasound image frame" as referred to herein is synonymous with a 2D ultrasound image.

Figure 1:
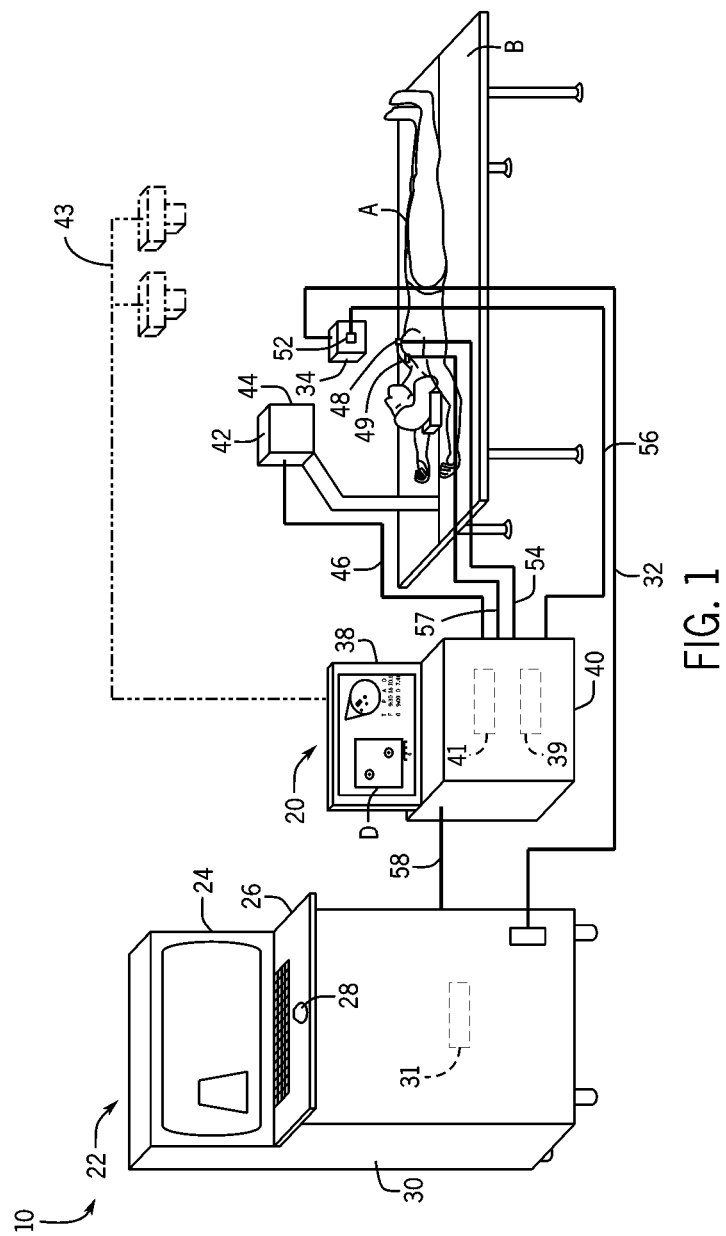
FIG. 1 depicts an overview illustration of an imaging system that includes an ultrasound device and a three-dimensional mapping display system (TDMD), according to an embodiment of the invention.

Turning to FIG. 1, a schematic illustration of an ultrasound system 10 incorporating three-dimensional mapping display system (TDMD) 20 is shown. Ultrasound system 10 includes an ultrasound machine 22 having a display 24, interface with keyboard 26 and pointer 28, chassis 30 containing operating hardware, which is referred to hereafter as a processor 31, probe connecting cord 32, and a handheld image data acquisition device or ultrasound probe or transducer 34. TDMD 20 is coupled to ultrasound system 10 by way of a video output cord 58. TDMD 20 may be deployed as an add-on to any existing ultrasound machine 22, and can outfit DICOM compatible and non-DICOM machines as well.

TDMD 20 includes a TDMD display 38, TDMD chassis 40 containing hardware, which is referred to hereafter as a processor 41, having programmed thereon software (described in detail below), a storage device 39, 3D magnetic tracking member 42 with the transmitter 44 connected to TDMD 20 by 3D magnetic tracking member cord 46. While both ultrasound machine 22 and TDMD 20 are illustrated as having individual displays 24, 38, it is contemplated that the visual outputs of ultrasound machine 22 and TDMD 20 may be combined in a single display in an alternative embodiment.

According to various embodiments, TDMD Chassis 40 is a computer such as an off-the-shelf PC computer with Windows XP®, Windows 7 (by Microsoft Corporation, Redmond, WA) containing a processor 41 that is capable of running instructions compiled in C# and C++ languages. Alternatively, embodiments of the invention can be implemented with any suitable computer language, computer platform and operating system. Processor 41 is provided with a number of modules, described in detail in FIG. 2, which are programmed with software that is used to process the data received by the processor 41 from the sensors 48, 49, 52 and data received from the ultrasound machine 22 and carry out the real-time anatomical reference point tracking techniques described below that enable a user to accurately review, evaluate, and compare examination results by having anatomical reference(s) guides to isolate target sites. Processor 41 is also programmed with software to carry out the techniques discussed with respect to FIGS. 5, 6, 8, 9, 12, 13, 19, and 20. In an alternative embodiment, processor 41 may also be programmed with image reconstruction software that would permit TDMD 20 to receive data directly from the ultrasound transducer 34 and reconstruct ultrasound images therefrom.

Figure 5:
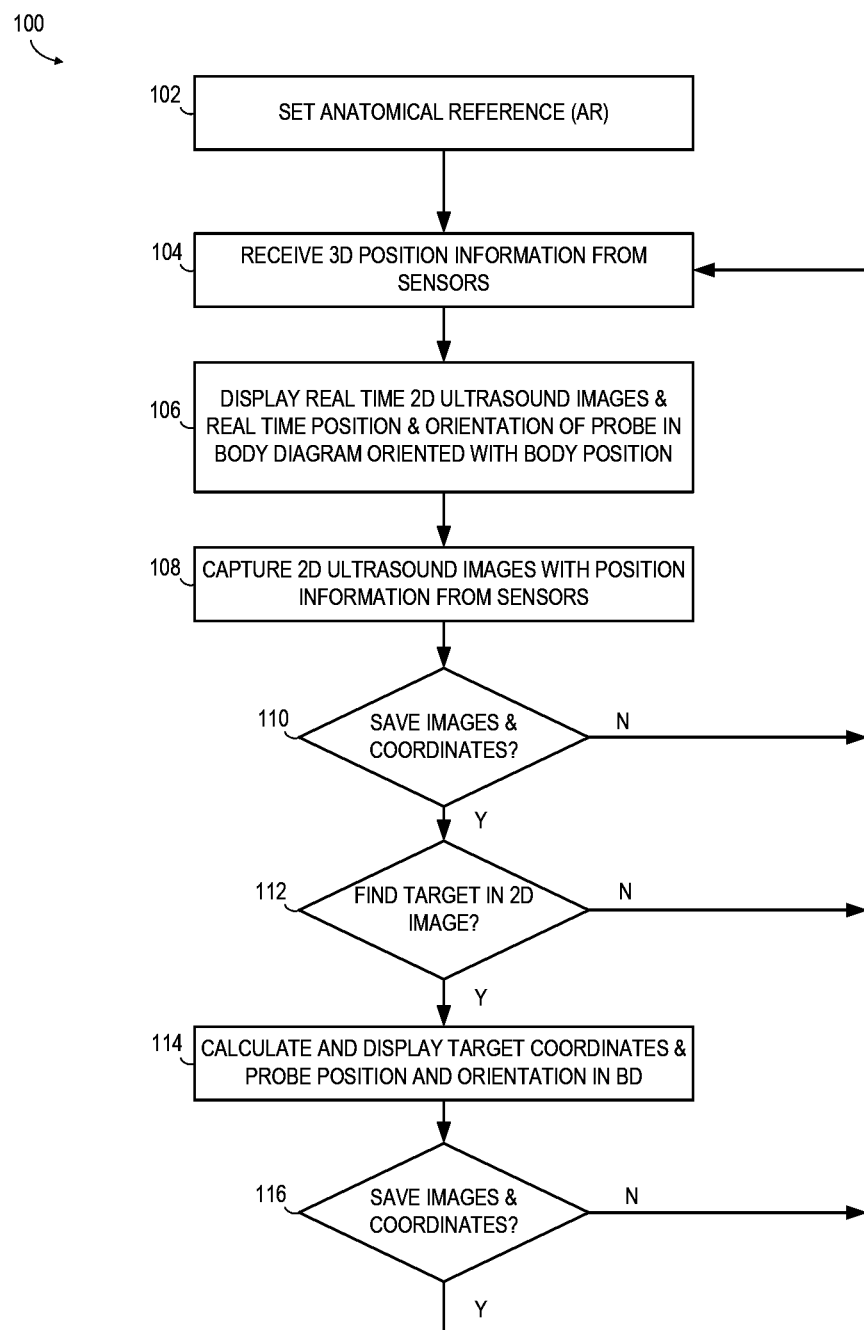
FIG. 5 is a flow chart illustrating the steps of a technique for measuring and recording the positional information associated with the diagnostic ultrasound images using a first position sensor for anatomical reference tracking and a second position sensor for body position and orientation tracking.

A first anatomical reference sensor or marker 48 is connected to TDMD 20 by a cord 54 and is used to monitor the position of a first anatomical reference (AR) point on the patient's body A, such as the nipple C, as described in more detail in FIG. 5. Optionally, a second anatomical reference sensor or marker 49 is attached to track the patient's body position in reference to the examination table B and is connected to TDMD 20 by a cord 57. In the exemplary embodiments described below, sensor 49 is attached to a chest wall structure, such as, for example, the sternum. Another sensor 52 is connected to ultrasound probe 34 and to TDMD 20 by a cord 56. In one embodiment sensors 48, 49, and 52 are magnetic sensors such as, for example, magnetic sensors manufactured by Ascension Technology, Burlington, VT, which are capable of being tracked in three dimensions.

In an alternative embodiment, sensors 48, 49, and/or 52 are of a wireless variety, thus sensor cords 56, 57, and/or 58 may be omitted. Also, a combination of wired and wireless position sensors can be used to provide the position tracking module with positional information from tracked landmarks or anatomical reference (AR) points on the patient's body A and the ultrasound probe 34. In yet other embodiments, elements 48, 49, and 52 are markers that may be tracked using an optional overhead infrared or optical AR tracking system 43 (shown in phantom), which incorporates one or more infrared or optical cameras. In such an embodiment, sensor cords 56, 58 would be omitted. When used, AR tracking system 43 may comprise at least one infrared camera, such as, for example, those commercially available (Natural Point Inc., Corvallis, OR), with the dedicated hardware and software receiving reflected infrared light from the reflectors or emitted infrared light from small infrared light sources applied over the anatomical references. The infrared cameras can be replaced with optical cameras and the infrared reflectors or emitters with optical markers or light emitters.

While various techniques are described herein for tracking the ultrasound probe 34 and one or more anatomical reference points on the patient's body in real time during an ultrasound examination, real-time tracking is not limited to the above solution, but other tracking modalities like ultrasound, optical, inertial, and the like can be used for the ultrasound probe and optical/pattern recognition, magnetic, etc. for the anatomical reference point real-time tracking. It should also be noted that tracking modalities can be used in combination with one another, for non-limiting example, ultrasound tracking with optical tracking. It is also noted that the described TDMD 20 and method can optionally be used with the anatomical reference tracking feature disabled.

As described below, sensors 48, 49, 52 are used to dynamically track the ultrasound probe 34 and one or more AR points on the patient's body A. The positional data received by TDMD 20 from sensors 48, 49, 52 is processed by processor 41 and used to co-register the ultrasound real-time images acquired by ultrasound machine 22 with a body diagram or other secondary sets of acquired ultrasound images, to provide real-time position and orientation information about the ultrasound probe 34, image frames, and the examined region of the patient's body A. Additional sensors or markers (not shown) may be included within TDMD 20 to track additional AR points on the patient's body A. According to various embodiments, TDMD 20 may be configured to continuously track one or several anatomical reference markers or sensors. If multiple anatomical reference markers or sensors are used, TDMD 20 may track some or all of the markers or sensors continuously.

To ensure reproducible and accurate mapping of the ultrasound images, sensors 48, 49, 52 are attached at well-defined and reproducible sites, outside or inside the body A and on the ultrasound probe 34, respectively, during repeated ultrasound examinations.

Sensors 48, 49, 52 may be used simultaneously or singularly. As a non-limiting example, the sensor 48 is attached to the nipple C in the same position, such as the center of the top surface of nipple C, during repeated breast ultrasound examinations, as shown in FIG. 5.

Figure 2:
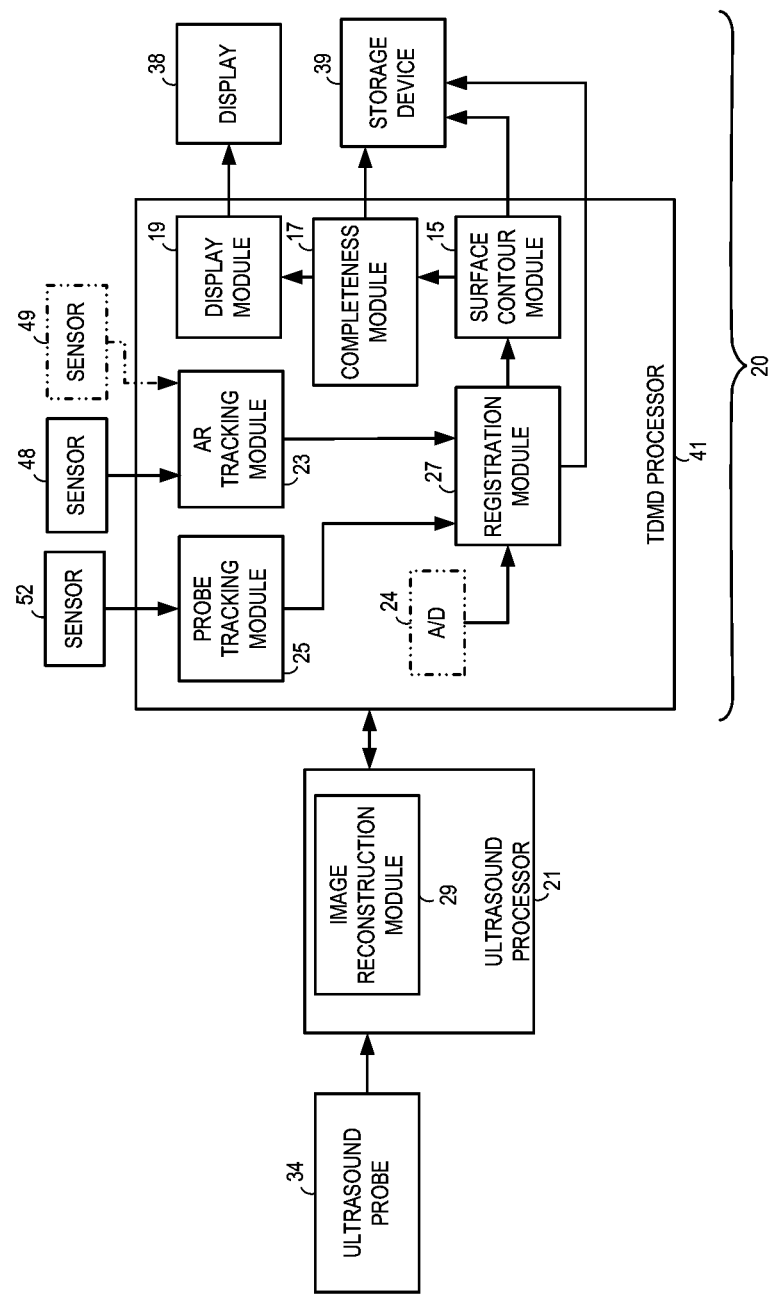
FIG. 2 is a functional block diagram of the imaging system of FIG. 1.

Referring now to FIG. 2, a functional block diagram illustrating the various general working aspects of TDMD 20 of FIG. 1 is shown. Positional data from sensors 48 and 49 is received by an anatomical reference tracking module 23 or board of processor 41. Likewise, positional data from sensor 52 is received by a probe tracking module 25 or board of processor 41. Modules 23 and 25 process the received data and provide the data to a 3D position registration board or module 27 of processor 41. Also provided within processor 41 is a surface contour module 15, which generates a breast surface contour, and a completeness module 17, which generates a completeness map of the acquired image data, and a display module 19. The functionality of modules 15, 17, 19, and 27 are discussed in more detail below with respect to FIGS. 5, 6, 8, 9, 12, 13, 19, and 20.

Processor 21 of ultrasound machine 22 includes an image reconstruction module 29, which receives ultrasound data acquired via ultrasound probe 34 and generates or reconstructs 2D or 3D ultrasound images therefrom. The images are then provided to processor 41 of TDMD 20. In embodiments where ultrasound machine 22 generates analog images, an optional analog to digital video output module 24 (shown in phantom) is provided within processor 41 to digitize images received from ultrasound machine 22. One skilled in the art will recognize that video output module 24 may be omitted in embodiments incorporating an ultrasound machine 22 capable of providing digital images to TDMD 20. Registration module 27 of processor 41 receives the digital ultrasound images, associates the associated positional information from sensors 48, 49, 52 with the image frames and/or a body diagram, and outputs the information to TDMD computer display 38 and/or to a storage device 39 for review and processing at a later time. TDMD display 38 is then enabled to show images D captured by ultrasound device 22 and associated positional data as collected from sensors 48, 49, and 52.

FIG. 3 is a schematic representation of a portion of the patient A, to illustrate exemplary positions of sensors 48, 49, and 52 during a breast ultrasound examination. As shown, sensor 52 is coupled to ultrasound probe 34 and sensor 48 is applied at the upper margin of the right nipple C. In alternative embodiments, sensor 48 may be centered on the nipple C or positioned at alternative locations on the patient body A. Likewise, sensor 49 may be positioned to track an alternative anatomical reference point on the patient's body A such as, for example, the sternum. Sensor 48 continuously tracks the anatomical reference position, the nipple C in this case, to compensate for motion registration errors during the ultrasound examination.

FIG. 4 illustrates TDMD display 38 having displayed thereon image D from the ultrasound machine 22 and the body part diagram I corresponding to FIG. 3, with the position and orientation of ultrasound probe 34 at the time of image capture D represented with icon E. The location of two different targets F and G are depicted in body part diagram I. The corresponding position of these targets are illustrated as F' and G' in image capture D. Additionally, each target F and G is displayed with the associated position (clock face position with hourly representation or degrees to longitudinal axis and anatomical reference as center) and distance (cm) from the selected anatomical reference. Positional coordinates are displayed under body part diagram I in FIG. 4. While TDMD 20 may display any number of coordinates, the non-limiting example in FIG. 4 illustrates the position of targets F and G in reference to the nipple C in hourly format (here, 9:30 for F and 9:00 for G), position from nipple C in degrees (here, 15° for F and 0° for G), and distance from nipple C in centimeters (cm) (here, 10.5 cm for F and 7.41 cm for G). When anatomical reference sensors 48 and 49 are used to dynamically track the position of the nipple C and patient's body A, the clock face position can be calculated in reference to the real-time patient's body orientation planes, which would increase the accuracy and reproducibility of measured targets positional coordinates.

Figure 7:
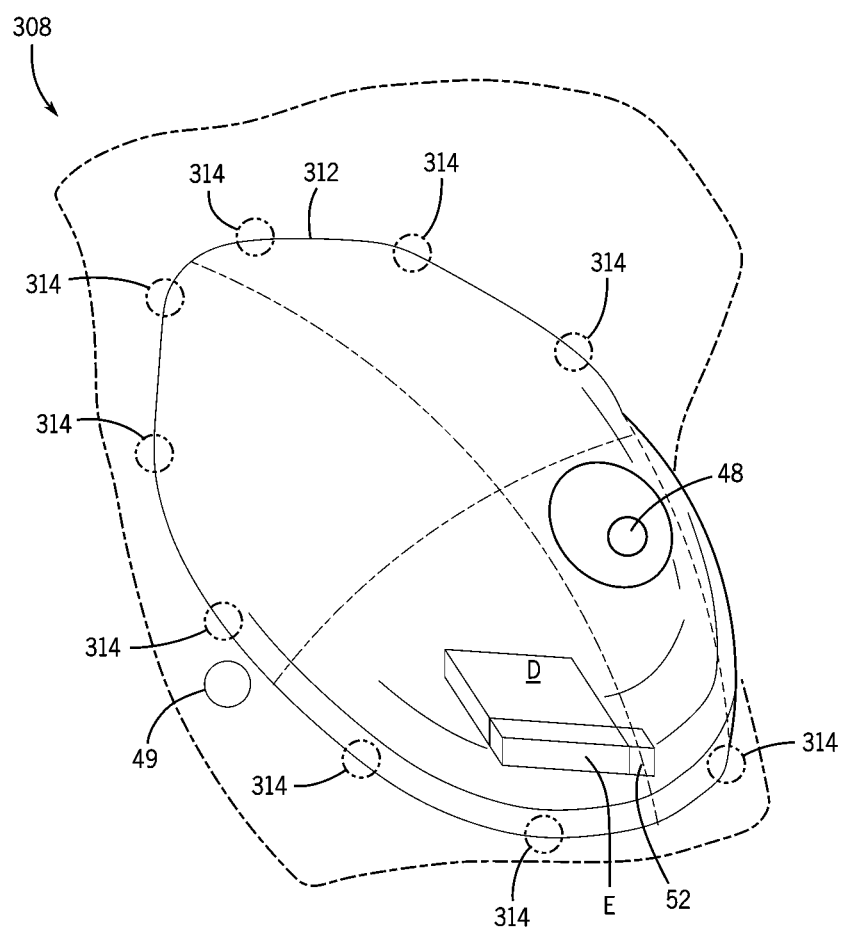
FIG. 7 is an exemplary breast diagram illustrating the position of the breast surface contour, anatomical reference sensor, body sensor, and calibrated ultrasound probe, according to an embodiment of the invention.

While represented as such in FIG. 4, the body diagram I is not limited to the two-dimensional (2D) "bird's eye view" type like the "clock" representation for the breast, but more complex and realistic three-dimensional (3D) representations of the body or body regions, including images obtained with other modalities like MRI, mammograms, gamma cameras or positron emission tomography and using contour rendering algorithms, can be used. The calculated and recorded positional data can be displayed in these representations. An exemplary 3D body diagram is illustrated in FIG. 7. Additionally, the position and orientation of ultrasound probe 34, can be depicted in a realistic appearance in space so it can be easily reproduced at subsequent examinations.

The position of a small tumor or other target in the breast, or other body part, depends on the patient's body position due to the gravity effect and the position and orientation of the ultrasound probe 34, which can displace the tissue under the probe 34 when pressure is applied by the operator on the ultrasound probe 34. To obtain accurate reproducible positional coordinates of a target or lesion from one examination to a subsequent examination, TDMD 20 measures the position and orientation of the ultrasound probe 34, monitors the patient's body position and orientation via sensor 49 and displays it as icon BO (FIG. 4), and monitors for movement of deformable tissue via sensor 48 in real time during an examination.

Referring now to FIG. 5, an operating technique 100 for TDMD 20 that includes the steps for recording the 3D position of targets in relation to one or more anatomical reference(s) is shown. For each patient A, at the beginning of examination the spatial position of the anatomical reference(s), patient's body position and the ultrasound probe position relative to anatomical reference(s) and its orientation relative to the body anatomical planes are defined in a spatial coordinate system and recorded at step 102. This step provides the reference for the co-registration of the ultrasound probe 34 and acquired ultrasound images with the body diagram or secondary set of images acquired during a subsequent examination. One method is to hold the center of the scan head 35 of the ultrasound probe 34 fitted with position sensor 52 at the anatomical reference point, for example, on the Nipple C, in a known orientation with the patient's body planes and axes, for example sagittal plane, horizontal, parallel to the patient A and parallel to the long axis of the examination table B to determine the patient's position and orientation axes and planes. In this step the nipple C position is set with the position coordinates at the center of the ultrasound probe 34 and the known patient's plane, such as, for example the sagittal plane, is set using the coordinates of the matching scan plane of the ultrasound probe 34. Initial calibration is also performed to register the scanning plane orientation and position of ultrasound probe 34 according to a known 3D calibration method.

At step 104, 3D positional information from sensor 48 (and sensor 49, if used) is received by processor 41 and used to track and record the position of the anatomical references (e.g., nipple C, sternum) based on the real-time position of the sensors 48, 49. Likewise, positional information from sensor 52 is received by the processor 41 and is used to track the real-time position and orientation of the ultrasound probe 34. In a configuration that uses two sensors 48, 49, the patient's body orientation planes may be set by holding the ultrasound probe 34 with the scan plane parallel with a known patient's plane Changes in the patient's body position and orientation during an ultrasound examination can have an effect on the measurement and description of a lesion's position. During the real-time ultrasound examination image acquisition and capture, each internal ultrasound target position relative to the anatomical references depends, among other factors, on the patient's position relative to the direction of the gravity force or the earth's magnetic field. Therefore the positional relation between the patient's body position and an examination table, B or other reproducible fixed reference used to position the patient A, a chair or a wall for example, can be associated with the ultrasound images or other images of the body, to aid repositioning the patient at subsequent imaging and match the gravity force effect between temporally distinct image sets. The gravity force effect is larger on deformable structures, like the breast. For example, during a breast ultrasound exam, the position of a small target in the breast relative to the nipple or other anatomical reference can change between the supine and half decubitus patient positions on the examination table. By recording the patient's body position during images, the patient whole body position may be adjusted in subsequent examinations to match the body position recorded with the previously obtained ultrasound images.

In an alternative embodiment, the output from the sensor 49 can be used to measure and set the body reference position and orientation with the patient's body positioned in the supine or other known reproducible body position on an examination table B. After setting the patient's body reference planes in the spatial frame, the output from sensor 49 can measure changes in the body position and orientation during the imaging session and the patient's whole body position relative to the examination table B or other fixed reference object can be recorded for each 2D ultrasound frame.

Alternatively, the patient's planes and axes can be measured using multiple anatomical references with the patient's body holding in one position and orientation on the examination table B. For example, longitudinal and transverse axes of the patient can be initially determined by recording the position of a chest wall structure such as the sternal notch via sensor 49 and calculating the longitudinal and transverse axes of the patient in reference to the examination table or other fixed object, respectively. Sensor 49 is aligned with the patient's body planes and axes and follows position and orientation changes of the body planes and axes during imaging. The output of sensor 49 is registered with the positions of above-measured axes, planes or volume positions and the changes in the output of sensor 49 is used to calculate the patient's body axes or planes positions changes, which can be displayed in reference to another reference object, like the examination table B. Alternatively, the positional changes from the sensors 48, 49 attached to the patient A are applied to the patient body coordinates to display the whole body position change relative to the examination table or other fixed reference. The positional change output from the sensors 48, 49 is applied to calculate the patient's planes position and orientation, and recorded with corresponding ultrasound images. The patient's real-time body position during imaging (BO, FIG. 4) can be represented as the orthogonal imaginary axes and planes used to represent the whole patient body position, coronal plane, sagittal plane, axial plane or any other conventional representation.

Additionally, the rotation around the initial position of axes and planes can be graphically represented and recorded. The recorded body position from one or more previous images can be displayed in real time during a subsequent examination and used to reposition the body in the same position the previous images were obtained, to help produce the images in the same orientation and directions as those of previous images and help the relocation of previously detected targets and other associated findings with known positional coordinates relative to the anatomical references. Alternatively, if differences exist between the body position recorded with the previous images of same body region, the positional difference can be applied at the previous set of images to adjust the previous set of images positional data and display to guide the operator to match the real-time images, with the previous set of images. This technique can be applied with a set of previously-acquired images and current images during scanning or to multiple sets of previously-acquired images to realign image sets recorded at different times.

These and additional methods for registering and recording the patient's body position are described in detail in U.S. Ser. No. 13/719,200, the disclosure of which is incorporated herein by reference. With any method used for the patient's body position tracking, the recording of the patient's whole body position and orientation can be automated using TDMD 20 by tracking and recording the position coordinates of one or more anatomical reference sensors attached to the patient's body and compared with a reference body's position coordinates. The real-time or recorded images D can be displayed with the corresponding body position relative to the examination table B or other object in a body orientation diagram BO, together with the body diagram used to represent the relative position of the ultrasound probe 34, scanning plane, body diagram and any recorded targets, as shown in FIG. 4.

Continuing with the discussion of FIG. 5, at step 106 the position and orientation of ultrasound probe 34, as determined by the output of sensor 52, and the position of anatomical reference(s), as determined by output of sensor 48, 49, are continuously displayed in TDMD display 38 or ultrasound display 24, as a moving icon, E or the actual ultrasound frame D over the body part diagram or other representation, in relation to one or more anatomical reference(s), nipple C or others, as illustrated in FIG. 4.

For a realistic representation of the body map and ultrasound probe icon and frame at the same scale, the body diagram or other body representation can be calibrated to match the size of ultrasound probe 34. In one non-limiting example the radius of the breast can be measured and used to calculate the size of the body diagram at same scale with the ultrasound frame representation. In another non-limiting example, the position coordinates of multiple points at the margins of the breast or other structure can be measured and used to fit a 2D or 3D shape of the breast or other structure to be used as the body diagram with TDMD display 38.

At step 108, responsive to a command from the operator to "freeze" a 2D still image of interest or capture video cine loops or 3D images, the current image or video clip is frozen or captured and subsequently saved at step 110 in TDMD computer 40 or a host computer with the position and orientation of the patient's body and positional information associated with ultrasound probe 34 and sensors 48, 49 to each frame or set of frame images.

The position of each pixel in an ultrasound image or voxel in the volume images in reference to the anatomical reference(s) is calculated from 3D positional data received from sensor 52 and corrections applied to the anatomical reference(s) based on the 3D positional data received from sensors 48, 49. The positional information of ultrasound probe 34 is displayed for each image is presented in alphanumerical format as distance and angle from the anatomical reference, hourly or clock face position coordinates, as shown in FIG. 4. Additional data fields are also available, including the position of the patient during the examination (supine, lateral decubitus, or any other position, etc.).

At step 112, a target may be located in an ultrasound image, either manually by an operator by pointing to the target (image pixel/region of pixels) with a pointing device in the image displayed on TDMD display 38 or ultrasound display 24 or using an automated detection algorithm. The coordinates associated with the target are calculated at step 114 in relation to anatomical references and displayed in combination with the orientation and position of the ultrasound probe 34 in the body diagram at the time of the ultrasound examination or at a later date. In one embodiment, the position of a target is assigned an hour from 1 to 12 o'clock, clock face position, when the region (breast or abdomen) is viewed from above as a clock, with the anatomical reference, nipple C or umbilicus respectively, imagined in the middle of the clock and also as a graphic diagram of the region, as shown in FIG. 4. The clock face position can be calculated to represent the projection on the patient's real-time coronal plane, as determined from the tracked position of the patient's body. The graphic diagram points to the relative position of a target over a body diagram of a body part, the breast, for example. Accordingly, multiple targets can be selected/displayed or erased. The target position can also be determined at a later time in TDMD computer 40 or a remote computer programmed with TDMD software, from the saved ultrasound images with the associated positional information. TDMD computer 40 allows for the manual or automatic entry and display of target coordinates from previous exams over the body diagram or body part diagram, with the position and orientation of the ultrasound probe icon E in relation to the anatomical reference(s) and body axis, represented in real time in the graphic diagram. This feature allows for ultrasound device operator orientation and guidance to help moving ultrasound probe 34 and find and examine a known target from a previous examination. The images and associated positional information are saved at step 116.

The positional information of targets and anatomical references obtained using TDMD 20 can be used to display the original or processed 2D or 3D ultrasound images over a real-time co-registered body diagram, map or other 2D or 3D set or sets of body images. The displaying of the ultrasound images over other co-registered body diagrams or other images can be performed in real time, to guide the ultrasound operator during scanning, or at a later time on a local or remotely located image viewer. The real-time or near real-time display of ultrasound images, described above, can be performed at the local computer or at a remote viewing station or stations, where the images from the local computer are immediately transferred to the remote interpretation stations over a network system, internet connection or any other connectivity system. The remote viewer can review the transferred images in near real time or at a later time and provide feedback to the ultrasound operator regarding the ultrasound examination in progress or after its completion. The remotely transferred ultrasound images can be stored at remote or local locations.

TDMD 20 enables the recording of 2D frames in a video sequence (clip) or cine loop, with each frame saved with the real-time positional coordinates relative to one or more anatomical references, such as nipple C, as described above. Then using the positional information in the multiple 2D frames of one or more video sequences corresponding to a scanned volume, the 2D images can be reconstructed in 3D volume images corresponding to the scanned region, using known 3D reconstruction algorithms. The 3D volume reconstruction can be obtained from the original captured 2D ultrasound images or the segmented or otherwise processed 2D images in a video sequence. Since the position of each 2D frame used to reconstruct the volume images is recorded relative to the real-time position of the anatomical references and patient body position and orientation, each voxel in the volumetric image set has associated positional coordinates calculated using the output of sensors 48, 49. Thus, the position coordinates of each selected voxel or voxels can be accessed, corrected with respect to the patient body position, orientation and tissue movements during scanning, and displayed.

Since each 3D set of images contains positional information from the source 3D images in relation to the anatomical reference position and patient body orientation, one or more 2D or 3D sets of images can be displayed over the body diagram at the same time. The associated position and orientation of ultrasound probe 34 can be displayed along with the anatomical references on the images. Additional positional references may be represented by same structures detectable in multiple images or image sets, sensors or markers with known positional coordinates. The co-registration of the ultrasound images with other body maps or images can be performed during scanning the patient or at a later time, at a local or remote computer. Accordingly, the 3D positions of individual ultrasound frames, multiple ultrasound frames or corresponding reconstructed volume or volumes obtained with TDMD 20, can be registered with and represented over a body diagram or body part diagram, including realistic maps obtained from the patient's measurements, real patient photographic data or other imaging modality data like CT, Mammograms, MRI, PET, SPECT, etc.

When the free hand ultrasound is used to obtain video sequences for direct review or 3D reconstruction, the probe speed over the skin and the probe orientation are important factors for the quality of the 3D reconstructed images. A constant probe movement with the speed matched to the ultrasound frame rate and the scanning plane of each 2D frame parallel to each other, in multiple consecutive frames, is desirable for accurate 3D volume reconstruction or recording of successive 2D frames in video clips at short uniform distance between the frames to allow the detection of small targets. The real-time scanning plane can be visualized during scanning, displayed over the body diagram and the operator can adjust the probe position as needed to obtain good quality 2D images. The ultrasound 2D image plane position and orientation in consecutive frames can be compared and the angles between the axes in consecutive planes calculated and displayed, with warnings set when exceeding the predetermined range for an accurate 3D reconstruction. An on-screen indicator can show the real-time ultrasound probe speed and guide the operator to maintain the probe speed within the recommended range for the ultrasound machine settings.

To assess the completeness of ultrasound scanning with TDMD 20, the position of the region of interest (ROI) or volume to be scanned is defined and measured relative to the selected anatomical reference(s), body position and orientation, and ultrasound probe 34 position and orientation using data output from sensors 48, 49, and 52, respectively. Subsequently, the position of the ROI can be tracked during an ultrasound examination using the position sensors with TDMD 20. In the case of a breast ultrasound examination, the ROI to be scanned is defined by mapping the breast surface contour using TDMD 20 in order to determine the skin surface area to be covered by the operator with ultrasound probe 34 during an examination. As used herein, "breast surface contour" refers to the outline of the surface area of the breast tissue at the chest wall and represents the bottom surface of the breast. In other words, the breast surface contour, with the area within it, is the boundary between breast tissue and the chest wall structures underneath the breast.

Figure 6:
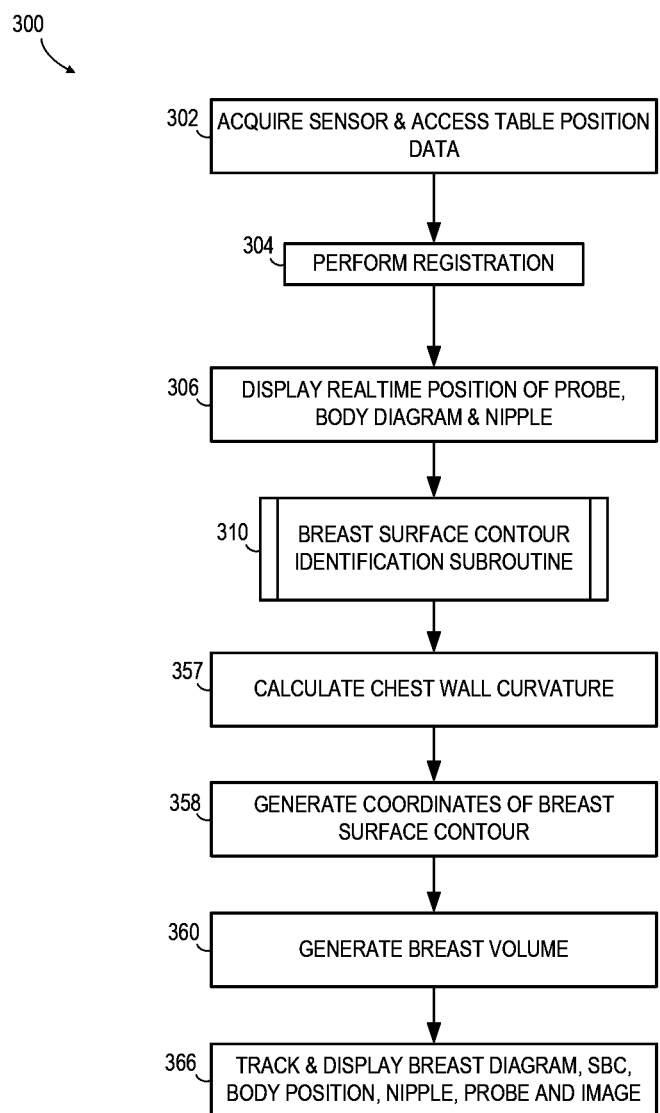
FIG. 6 is a flowchart illustrating a technique for generating a breast surface contour, according to one embodiment of the invention.

FIG. 6 illustrates a technique 300 for generating a breast surface contour according to one embodiment of the invention. Technique 300 begins at block 302 by acquiring data from one or more sensors and, optionally, accessing positional coordinates of the examination table B (FIG. 1) or other fixed object. According to alternative embodiments, technique 300 may acquire data from position sensor 52 coupled to calibrated ultrasound probe 34, at least one body position sensor, such as, for example, sternum sensor 49, or a combination of two or more sensors attached to the patient's skin, such as, for example, sternum sensor 49 and an anatomical reference sensor 48 attached at the nipple C.

The acquired sensor data and table position coordinates (if used) is used at block 304 to register the patient's body position relative to the examination table B or other fixed object in the manner discussed above. At block 306 the real-time position of ultrasound probe 34, anatomical reference sensor 48, which represents the position of the nipple C, body diagram I, and body orientation diagram BO, which depicts the real-time position and orientation of the patient A, are displayed to an operator on display 38 in a similar manner as depicted in FIG. 4.

In one embodiment, the displayed body diagram is a 3D breast diagram 308 as illustrated in FIG. 7. As shown, 3D breast diagram 308 is a graphical representation of a portion of the patient A that includes the breast BR and icons that represent the position of the anatomical reference sensor 48 located at the nipple C and the body sensor 49 located at the sternum. An icon E representing the position and orientation of ultrasound probe 34 is also displayed. In one embodiment, the relative orientation of ultrasound probe 34 is depicted by displaying the location of the calibrated sensor 52. The relative position and orientation of the current ultrasound frame D is also displayed in the 3D breast diagram 308. While FIG. 7 displays a 3D breast diagram, it is contemplated that the relative locations of ultrasound probe 34 and sensors 48, 49 may be displayed in a 2D breast diagram similar to that shown in FIG. 4.

Referring again to FIG. 6, and with continued reference to FIG. 7 as appropriate, at block technique 310 enters a subroutine wherein the breast surface contour 312 is identified and registered with the position and orientation of the patient's body A and position of the nipple C. The breast surface contour 312 is defined by mapping the breast border at the chest wall using TDMD 20 while the patient A lies still on the examination table B.

According to one embodiment, the breast surface contour identification subroutine 310 is carried out by recording the tracked position of ultrasound probe 34 at a multitude of points at the breast surface contour 312. This task may be performed by sliding ultrasound probe 34 over the skin at the breast limits to generate a surface breast contour breast surface contour 312 at the chest wall and tracking the position of ultrasound sensor 52. A calibrated point at ultrasound probe 34, such as, for example, the center of ultrasound probe 34 or one extremity may be used to follow the breast surface contour 312 and record the calibrated point position relative to the patient's body position and orientation, tracked by sensor 49, at a fixed or variable frequency. Alternatively, a calibrated stylus, operator's calibrated finger or other calibrated object can be used to draw the limits of the breast surface contour 312 at the chest wall. The positions of the multiple points of the breast surface contour 312, as determined by movement of the calibrated ultrasound probe 34 or other calibrated object, are subsequently linked to generate the breast surface contour 312 at the chest wall, which is registered with the patient body A.

In an alternative embodiment, the breast surface contour identification subroutine 310 is carried out using a plurality of optional markers 314 (shown in phantom) attached to the skin of the patient A, as illustrated in FIG. 7. According to various embodiments, markers 314 may be reflective markers, active LED markers, infrared or optical elements. The relative position and changes in the breast surface contour 312 may be measured and tracked with 2D or 3D coordinates using an overhead tracking system, such as, for example, overhead tracking system 43 or overhead camera (FIG. 1). Alternatively, a reflective ink line drawn along the breast surface contour 312 may be used to define and track the breast surface contour 312 using TDMD with the overhead camera system 43 of FIG. 1.

In the above-described embodiments where the breast surface contour 312 is defined by tracing the outline of the breast using a calibrated object, reflective markers, or a reflective ink line, the elevation of the breast surface contour 312 is defined based on the position of the scan head 35 of the ultrasound probe 34. As such, the accuracy of the determined elevation of the breast surface contour 312 will be dependent on the operator's skill and on the thickness of fatty tissue thickness above the chest wall at the breast surface contour 312. Possible error introduced by using these methods may optionally be minimized by adjusting the elevation of the breast surface contour 312 based on the position of the interface between the chest wall and breast tissue in the acquired image frames that correspond to the location of the breast surface contour 312. In such an embodiment, image frames that contain the breast surface contour 312 will be identified and the elevation of the breast surface contour 312 will be lowered to the elevation of the chest wall/breast tissue interface in the image frames as appropriate.

Figure 8:
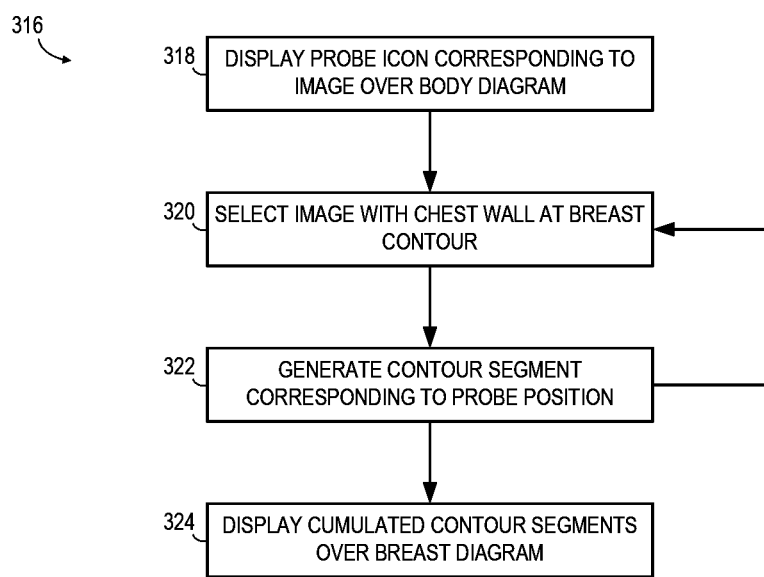
FIG. 8 is a flowchart illustrating a subroutine for identifying a breast surface contour, according to one embodiment of the invention.

In yet another embodiment, the breast surface contour identification subroutine 310 involves detecting the proximity of the chest wall to the scan head 35 that corresponds to closest position to the breast with no breast tissue interposed between the scan head 35 and chest wall and marking the position of the scan head 35 relative to the sternum sensor 49. FIG. 8 illustrates one exemplary technique 316 for detecting the position of ultrasound probe 34 that satisfies these conditions by directly marking the image as "chest wall." In a given ultrasound sweep that traverses the breast surface contour 312, one image frame from the sweep will contain the breast surface contour 312. Accordingly, at block 318 an icon depicting the position of ultrasound probe 34 corresponding to the image is displayed over the 3D breast diagram 308. At block 320 the operator selects the image with the chest wall only at the breast surface contour 312. A contour segment corresponding to the position of ultrasound probe 34 is generated at block 322. Blocks 320 and 322 are repeated until contour segments are generated that surround the entire breast. The generated contour segments are then cumulated and displayed over the 3D breast diagram 308 at block 324.

Figure 9:
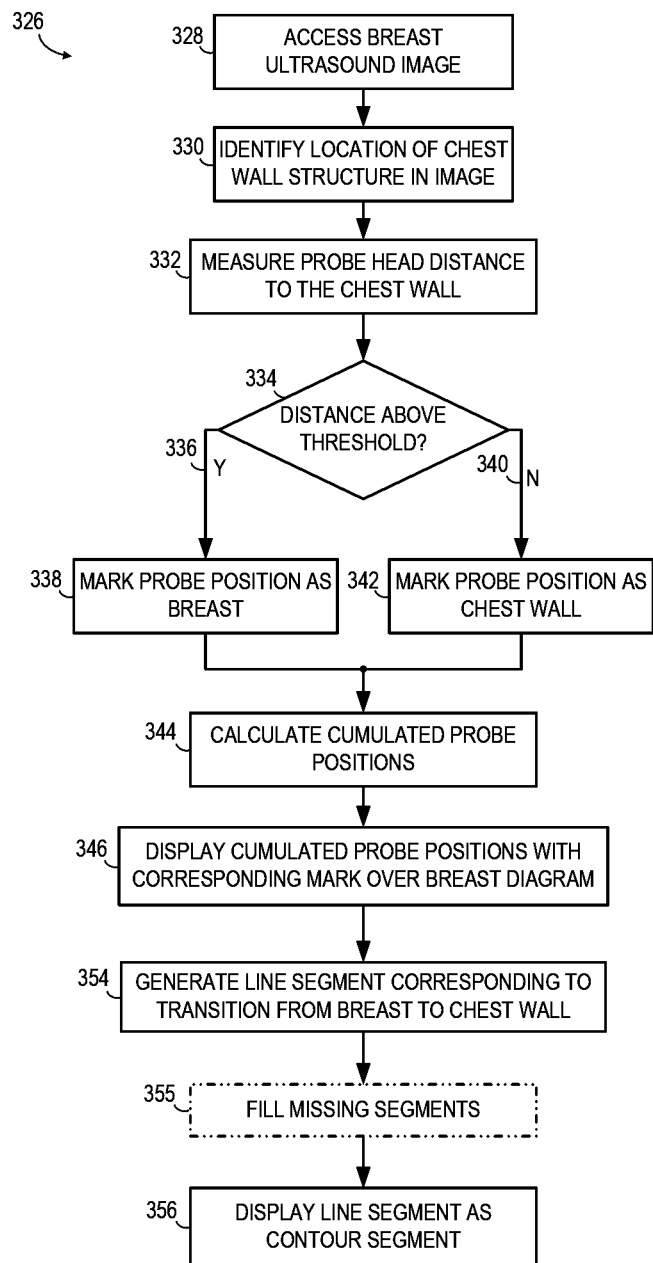
FIG. 9 is a flowchart illustrating a subroutine for identifying a breast surface contour, according to another embodiment of the invention.

FIG. 9 illustrates an alternative technique 326 for carrying out the breast surface contour identification subroutine 310 that includes generating the breast surface contour 312 at the interface between the breast and chest wall based on the location of a chest wall structure, such as, for example, a rib. Technique 326 begins at block 328 by accessing a series of breast ultrasound images acquired during a sweep of ultrasound probe 34. The location of the chest wall structure is identified in the image at block 330. In one embodiment, the location of the chest wall may be manually marked in an image by an operator. Alternatively, the chest wall is automatically detected with image processing software programmed with algorithms for chest wall detection.

Next, the distance between the head 35 of ultrasound probe 34, which is resting on the skin surface of the breast BR, and the chest wall is calculated at block 332. At block 334 technique 326 determines whether the calculated distance between ultrasound probe 34 and the chest wall structure is greater than a predetermined threshold. In one embodiment, this threshold may be a patient-specific value that is determined at the beginning of an examination by taking an image of the chest wall. If the distance is greater than the threshold 336, ultrasound probe position is marked as corresponding to the breast at block 338. If the distance is less than the threshold 340, ultrasound probe 34 position is marked as corresponding to chest wall at block 342. The cumulated probe positions corresponding to the breast contour are calculated relative to the chest wall sensor and displayed at block 344. Optionally, technique 326 includes a block 355 (shown in phantom) in which gaps are detected and filled between the generated contour segments. In one embodiment, any missing segments between the probe positions corresponding to the breast contour can be filled by TDMD 20 using an interpolation algorithm to obtain a continuous contour. Alternatively, if the number of probe positions is insufficient to generate a complete contour, TDMD 20 can prompt the user to continue scanning at additional probe positions.

Figure 10:
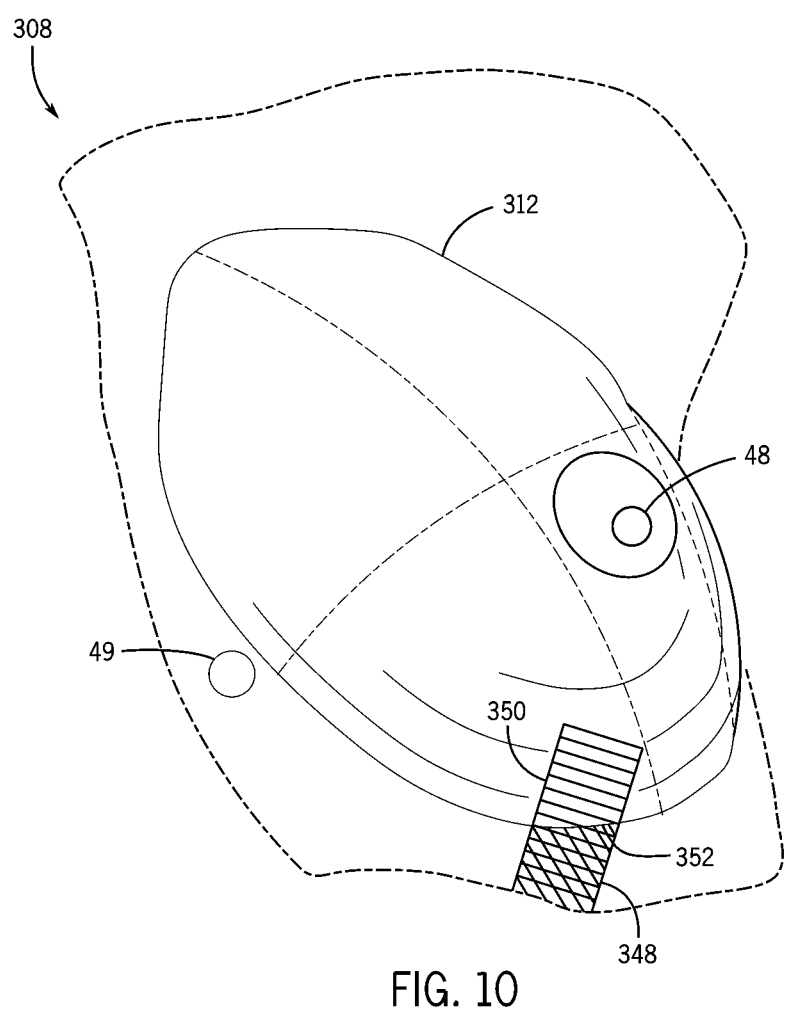
FIG. 10 is a 3D breast diagram having displayed thereon a generated line segment of the breast surface contour, according to an embodiment of the invention.

Referring now to FIGS. 9 and 10 together, in a next step 346 of technique 326, the cumulated probe positions marked as corresponding to chest wall 348 and the cumulated probe positions marked as corresponding to the breast 350 for the respective sweep are displayed over the 3D breast diagram 308. A line segment 352 corresponding to the transition from the breast to the chest wall is generated at block 354. The generated line segment 352 is displayed as a portion of the breast surface contour 312 at block 356. This series of steps is repeated using image data acquired from sweeps covering the remaining portion of the breast in order to generate line segments corresponding to the interface between the chest wall and breast. The generated line segments are combined to depict the overall breast surface contour 312.

Regardless of which of the above-described techniques are used to carry out the breast surface contour identification subroutine 310, the breast surface contour 312 is identified during scanning and may be superimposed on a 2D or 3D breast diagram 308 or any other graphical breast representation.

Referring again to technique 300 (FIG. 6), the chest wall curvature is also accounted for in calculations of the breast surface contour 312. The posterior aspect of the breast lays over the chest wall which is composed by the pectoral, intercostal muscles and the ribs. A complete breast scan ideally includes the whole breast tissue between the skin and chest wall. Therefore, technique 300 detects and documents the chest wall curvature and position relative to the ultrasound images at block 357. The chest wall is relatively fixed with the sternum and has a similar shape in most people. In one embodiment, technique 300 determines the chest wall positional coordinates by fitting a preexisting shape to the positional data associated with the sternum and the breast surface contour at the chest wall, as determined by TDMD 20. In an alternative embodiment, the chest wall position in the patient is mapped by identifying easily detectable chest wall structures in the ultrasound images, like the ribs, and calculating their positional coordinates with TDMD 20. After obtaining a sufficient number of coordinates, the chest wall can be reconstructed to fit the patient and can be displayed with the body or 3D breast diagram 308, breast surface contour 312, nipple point and ultrasound probe and image position and orientation dynamically referenced to the body planes and nipple point. Optionally, the chest wall surface can be continuously updated during scanning by determining additional positional coordinates at the chest wall from new images as they are acquired during the examination.

Once the initial position of the breast surface contour 312 is identified at the chest wall in the 2D or 3D space at block 310 and the chest wall curvature is determined at block 357, the positional coordinates of the breast surface contour 312 and the positional coordinates of the underlying chest wall surface, which defines the lower surface of the breast tissue, are determined at block 358. Thereafter, tracking of the position changes of the breast surface contour 312 during scanning can be done by directly measuring the position of breast surface contour 312 at short intervals of time with the same method used to measure its position at the beginning of the examination. Alternatively, once the position of the breast surface contour 312 is defined at the beginning of an examination, subsequent positional changes may be tracked with the body or sternum sensor 49, applying its position and orientation changes to the entire breast surface contour 312.

After the measurement of the initial positional coordinates of breast surface 312 and underlying chest wall surface, the total breast volume is determined at block 360.

In one embodiment technique 300 determines the total breast volume by generating a 3D volume above the positional coordinates of the breast surface contour 312 and underlying chest wall surface. The breast surface shape can be calculated and fitted from the positional coordinates of the breast surface contour 312, and underlying chest wall surface, and nipple C position and the body position/orientation as determined by sensors 48, 49. Thereafter, a preset breast shape can be fitted to the known positional coordinates. In a different embodiment, the breast skin area surface coordinates can be recorded in the 3D space at the beginning of an examination with overhead stereoscopic cameras or time of flight cameras and continuously tracked with the cameras or after the initial 3D registration of the breast surface to the nipple, body planes or other anatomical references. In yet another embodiment, the breast surface shape may be determined by tracking the elevation of the scan head 35 of the ultrasound probe 34 during a series of sweeps that covers the entire surface area of the breast skin within the breast surface contour 312. However, the breast surface shape generated using this method may contain inaccuracies due to the deformation induced by the ultrasound probe 34 as it presses on the breast skin during data acquisition. By determining the 3D breast surface shape, the breast volume can be rendered and calculated. Once the 3D breast surface shape is determined, TDMD 20 with attached skin sensors 48, 49 at the nipple and sternum, can apply deformation algorithms to fit the initial surface coordinates with the real-time anatomical reference positions to account for tissue movement during an imaging session.

When knowing the total breast volume, the total volume of multiple sequences of images obtained with ultrasound probe sweeps over the breast can be calculated from the positional information associated with each ultrasound image in each sequence of images and compared with the total breast volume obtained at the initial surface measurement to have a measurement of the entire breast volume coverage. In addition to being used to determine the completeness of scanning, the calculated breast volume values generated at block 360 can be used for other medical or non-medical purposes.

Figure 11:
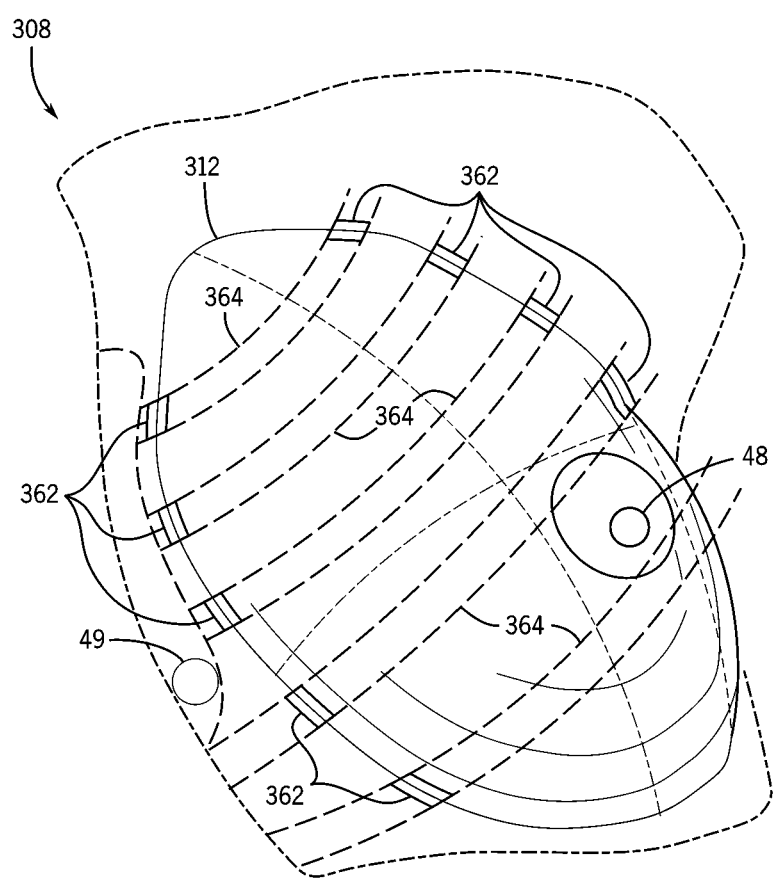
FIG. 11 is a 3D breast diagram having the chest wall displayed thereon, according to an embodiment of the invention.
Figure 12:
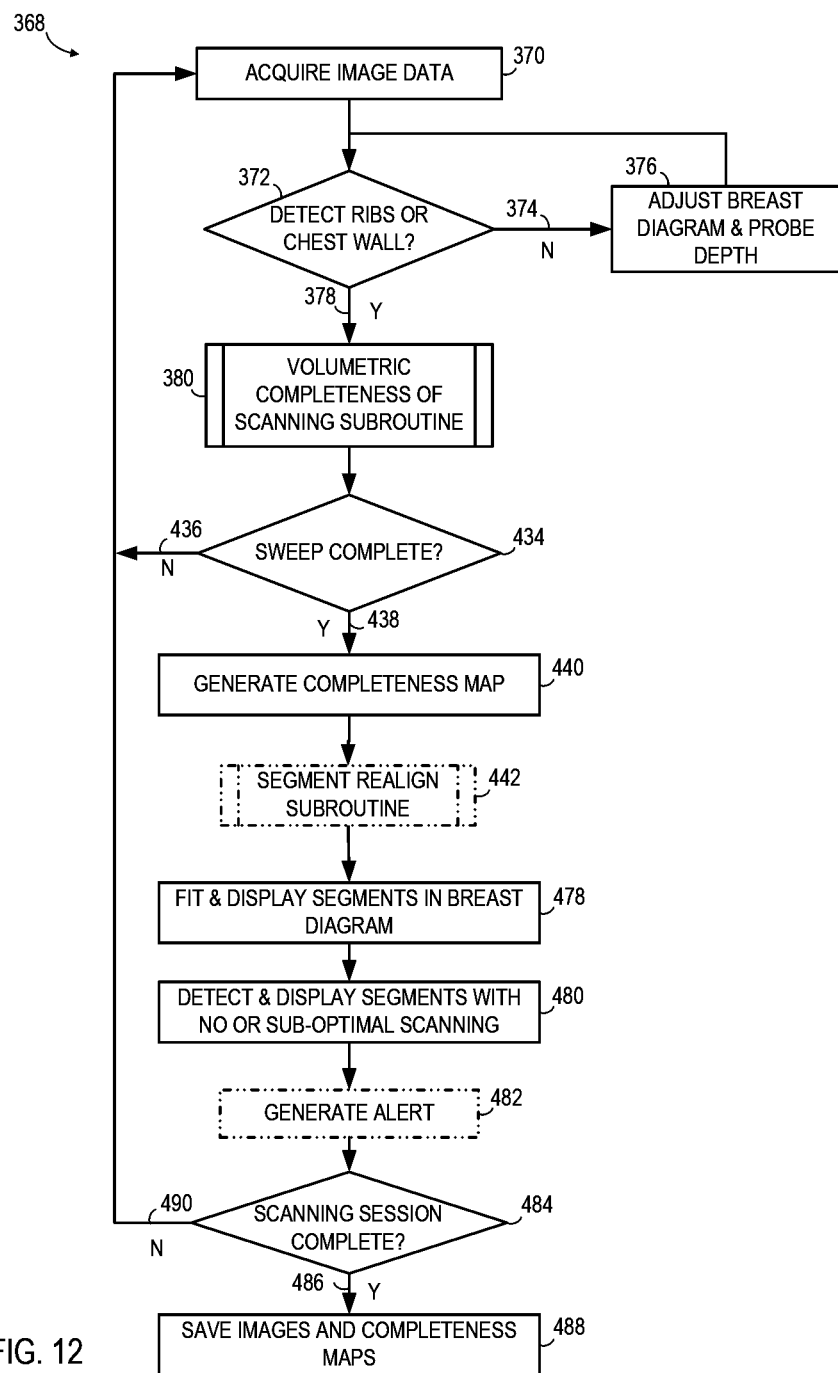
FIG. 12 is a flowchart illustrating a technique that evaluates the completeness of an ultrasound scan and generates one or more completion maps, according to an embodiment of the invention.

According to various embodiments, the ribs or chest wall detection can be performed manually by the operator or automatically with pattern detection algorithms in the images. The chest wall position may be determined by detecting the position of the ribs using image data acquired while scanning the chest wall with the calibrated ultrasound probe 34 around the breast and subsequently during the breast scanning. In one embodiment, the ribs are detected using data acquired using the calibrated ultrasound probe 34 to trace the breast surface contour during the initial mapping of the contour. As shown in FIG. 11, the position of the rib segments 362 that intersect the breast surface contour 312 may be used to estimate the geometry of the portions of the ribs 364 that lay underneath the breast tissue in one embodiment. Alternatively, pattern detection algorithms may be used to identify the ribs or chest wall using image data acquired from a scan that spans the entire breast surface area.

Referring again to technique 300 and FIGS. 6 and 7, at block 366 the breast surface contour 312 may then be displayed on the breast diagram 308 and/or stored for later use. A 2D or 3D breast diagram 308 is fitted to the generated breast area values and displayed in real time with the position of ultrasound probe 34, orientation and the breast surface contour 312, nipple point C, and body position and orientation on the examination table in real time to guide the ultrasound operator or, alternatively, may be recorded for later review. Since the position of the breast surface contour 312 is registered with respect to the chest wall, the breast surface contour 312 can be displayed over the 3D breast diagram 308 and used to determine ultrasound probe 34 position relative to the breast surface contour 312.

The breast surface contour 312 is relatively fixed to the body A, chest wall and sternum, since it is located at the skin covering a layer of fat and chest wall structures without interposed breast tissue. Therefore, the breast surface contour 312 is less susceptible to the breast deformation and will follow the chest movement. Body sensor 49 tracks the body position and when the breast surface contour 312 is dynamically referenced to the body sensor 49 attached at the sternum or other body part, the positional coordinates of the breast surface contour 312 follow the positional changes of body sensor 49 and corresponding chest and body position changes, regardless of the position of the nipple C as tracked by anatomical reference sensor 48.

During imaging the position coordinates of ultrasound probe 34 and images are tracked with body position sensor 52 relative to the nipple point using sensor 48 and to the body planes tracked by sensor 49, the breast surface contour 312 and body planes position and orientation are tracked by sternum sensor 49. Alternatively, the position and orientation of ultrasound probe 34, any of the anatomical references mentioned above, the nipple C position, sternum position/orientation and the breast contour position and orientation can be tracked with any position sensing devices like, but not limited to, magnetic tracking systems, overhead optical or infrared position tracking systems, time of flight cameras and other, alone or in any combination.

The breast skin surface contour mapping at the chest wall described with respect to technique 300 is only one example of surface mapping for a region of interest and does not represent a limitation of the method. Any region of interest can be mapped with a surface contour in the 2D or 3D space, including a part of the breast, axilla, neck, abdomen and other regions where the surface contour can be generated and its position recorded and tracked as described above.

In addition to determining the position and orientation of ultrasound probe 34 and image positions and orientations with respect to a region of interest such as a breast, it is desirable to assess any 2D areas or 3D volumes which were adequately or were not adequately evaluated with ultrasound images in order to prevent missing small lesions. Accordingly, a technique 368 for generating a map that depicts the completeness of an ultrasound scanning session is set forth with respect to FIG. 12. Technique 368 begins at block 370 by acquiring ultrasound image data. The position data of ultrasound probe 34, position data of nipple C, and patient body position and orientation data is registered to the acquired image data in the manner described above with respect to FIG. 6.

When assessing the completeness of scanning, it is desirable to detect ultrasound probe 34 positions and image frames associated with tissue images when ultrasound probe 34 is in contact with the skin, and exclude the images with ultrasound probe 34 removed from the skin with no tissue information. Accordingly, image data acquisition optionally may begin when contact between ultrasound probe 34 and the skin of a patient A is detected or based on an input from the operator. In one embodiment, ultrasound probe-to-skin contact is detected using proximity or pressure sensors that are attached to ultrasound probe 34. Alternatively, optical, infrared sensors or cameras or thermal sensors, similar to those described with respect to camera system 43 (FIG. 1), may be attached to the housing of ultrasound probe 34 perform the pattern recognition of skin images or temperature to detect the skin contact. In an alternative embodiment, the images containing tissue information (indicating probe-to-skin contact) are detected using pattern detection algorithms.

Unlike known ultrasound techniques in which an operator must manually set and adjust the depth of ultrasound probe for a scanning session, technique 368 automatically sets and adjusts the depth of ultrasound probe 34 during acquisition of image data to minimize the amount of image data that is acquired for areas outside the ROI (i.e., beneath the chest wall) and to determine the regions where the scan plane did not reach to the deep regions of the breast next to the chest wall. The chest wall is less deformable than the breast and its position and changes can be tracked with a sensor attached to the chest wall, like the sternum sensor 49. Once the chest wall surface is calculated and positionally tracked during the ultrasound examination, the position and orientation of ultrasound probe 34 is also known and the chest wall surface position in the ultrasound images can be calculated and displayed as illustrated in FIG. 11. When knowing the depth from the head of the ultrasound probe 34 to the chest wall surface, the ultrasound image depth may be adjusted to include the entire breast tissue region. At the same time the ultrasound frequency and number of focal spots can be adjusted to optimize image quality. Alternatively, when the ultrasound image depth does not reach to the chest wall, the unscanned gap can be detected, displayed and recorded, to guide the ultrasound operator during scanning or the information can be used at a later time.

In one embodiment, at block 372, technique 368 determines whether the acquired image data includes the chest wall. Ideally, the scan would acquire image data to a depth substantially equal to the chest wall. If the probe depth extends too far beneath the chest wall, extraneous image data will be acquired during the scan. If the probe depth is too shallow, some breast tissue may be missed during the scan. Accordingly, if the chest wall is not detected in the image data or if it is determined that the probe depth extends too far beneath the chest wall 374, the probe depth is adjusted at block 376 to reach the chest wall. On the other hand, if the chest wall is detected in the image data and it is determined that the position of the chest wall is relatively close to the inferior or bottom side of the ultrasound frame 378, technique 368 continues scanning and recording images at the current probe depth, and displays position and orientation of ultrasound probe 34 in real time on the breast diagram 308. If the depth of the ultrasound image is too large and includes too much image field beyond the chest wall and is beyond a set threshold, the depth is reduced to optimize including breast tissue in most of the field of view.

In an alternative embodiment where the position of the chest wall under the breast and the position of the scan head of the ultrasound probe 34 are known during scanning, technique 368 may be configured to calculate the distance between the chest wall and head of ultrasound probe 34 using the known positions. Thereafter, the calculated distance value would be used by TDMD 20 to determine a desired probe depth, which would then be compared to a current probe depth, and adjusted at block 376 if warranted based on the comparison. The probe depth adjustments initiated in either of the above-described manners may be made continuously or at predetermined intervals using a feedback loop between processor 41 of TDMD 20 and processor 31 of ultrasound machine 22, according to various embodiments.

At block 380 technique 368 enters a volumetric completeness of scanning subroutine during which technique 368 determines whether the consecutive spacing of the image frames acquired during one or more sweeps of ultrasound probe 34 is close enough to contain adequate image data for the scanned region. In an ultrasound sweep the multiple sequential images are displayed or recorded continuously, however the spacing between the line segments representing the scan head and the corresponding images in the scanned volume is dependent on the translational and rotational speed of the probe and the frequency the ultrasound images are obtained or the frame rate. Unless the frame rate and probe movement speed fall within an acceptable range, the individual images may be too spaced apart to prevent missing a small lesion or to provide good quality 3D reconstruction of the multiple images. Therefore, it is desirable to detect unacceptable gaps between sequential or neighboring images, so the ultrasound operator can be alerted to rescan the deficient region or record the gaps for rescanning at a later time.

Since the breast is connected to the chest wall, the deep breast region follows the movement of the chest wall, while the more superficial regions follow the nipple and superficial skin movement. Therefore, the breast tissue motion relative to the anatomical landmarks is not uniform, but gradually changes from following the nipple and surrounding superficial skin for the superficial regions to following the chest wall motion for the deep regions. Therefore, simply measuring the distance between frame to frame when scanning, would not give an accurate representation of the amount of tissue between the frames, since the tissue underneath the probe moves at a different speed compared with the deep breast tissue.

Figure 13:
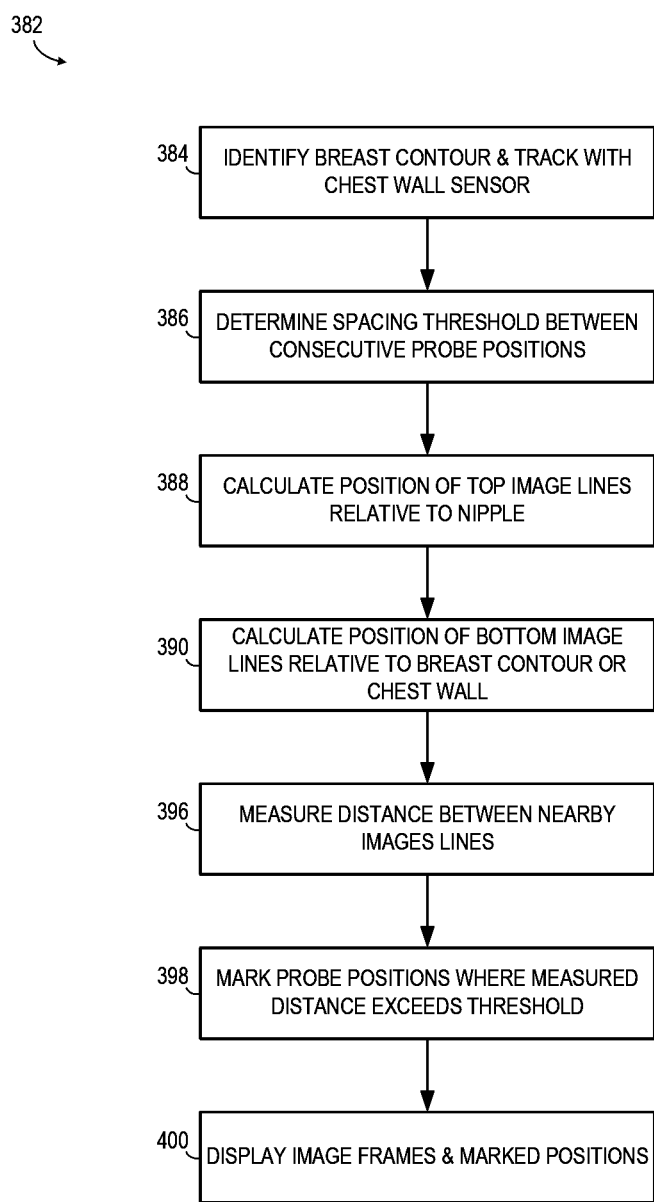
FIG. 13 is a flowchart illustrating a volumetric completeness of scanning subroutine, according to one embodiment of the invention.
Figure 14:
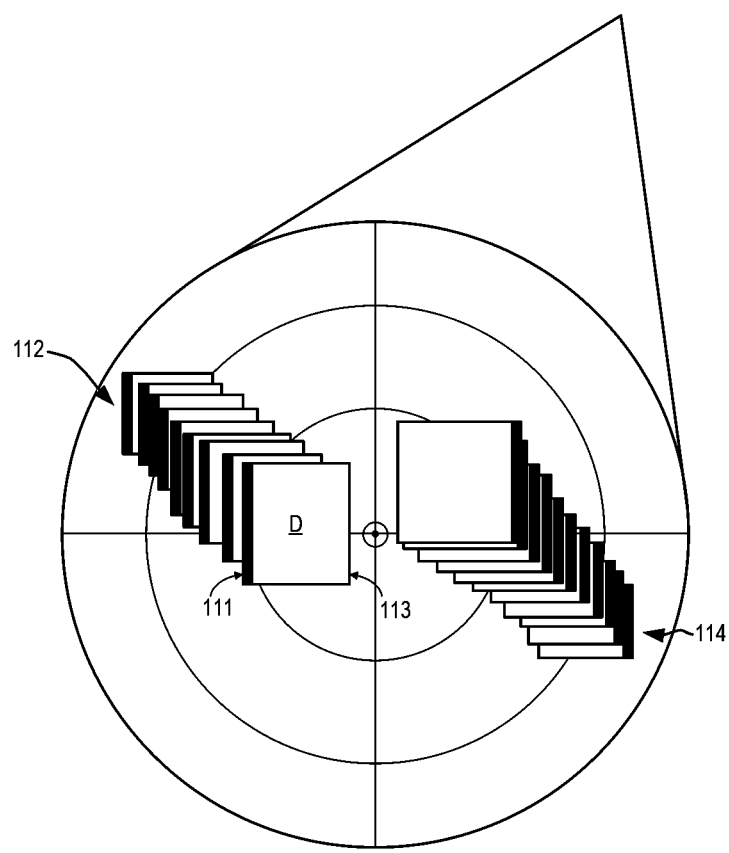
FIG. 14 is an exemplary breast diagram that illustrates the cumulated ultrasound probe positions with the thick line representing the surface of the head of the ultrasound probe and the opposite line representing the deep end of image at or close to the chest wall, for the images acquired during two sweeps.

FIG. 13 illustrates a technique 382 for carrying out the volumetric completeness of scanning subroutine, according to one embodiment of the invention. Technique 382 determines scanning completeness by mapping the near ends and far ends of the ultrasound images, measuring the distance between subsequent ultrasound probe scan head line and far end of the image segments, and detecting the segments where the distance measures more than the accepted threshold, as described in detail below. As used herein, "near end" refers to the end of the image frame directly underneath to the surface of the scan head (i.e., the end of the image immediately underneath the skin) and "far end" refers to the end of the image frame that is proximate to or includes the chest wall (i.e., the side of the image frame opposite the probe head). Representative near end 111 and far end 113 of image frame D are illustrated in FIG. 14.

Referring again to FIG. 13, technique 382 begins at block 384 by identifying the breast surface contour 312 in the manner described with respect to FIG. 6 and tracking the position of breast surface contour 312 using the sensor 49. At block 386, technique 382 determines an acceptable spacing threshold between consecutive positions of ultrasound probe 34. In one embodiment, the spacing threshold may be defined as a predetermined value, such as, for example approximately 2 mm. Alternatively, technique 382 may prompt an operator to input a threshold value.

Next, technique 382 accesses the co-registered image data acquired during a sweep of ultrasound probe 34 at block 388 and calculates the position of the near end of each ultrasound image frame acquired during the sweep relative to the position of the nipple C (as determined by anatomical reference sensor 48). At block 390, technique 382 performs a similar calculation to determine the position of the far end of each ultrasound image frame relative to the position of the breast surface contour 312 or chest wall. The position of the far end of the image frame will not be significantly changed by the positional changes of overlying breast, but will follow the body or chest wall position changes.

Therefore, a surface map of the positions of ultrasound probe 34 in reference to the nipple point and body orientation can be obtained with ultrasound probe 34 moved in one direction and a second map of the far end of the ultrasound images, or deep map, close to the chest wall, referenced to the body A only can be obtained at the same time. An exemplary chest wall surface map 392 and exemplary breast surface map 394 are illustrated in FIGS. 15 and 16, respectively, and discussed in more detail below. Because these two maps 392, 394 are generated from co-registered image data, the maps account for any motion of the deformable tissue and/or patient body that may have occurred during the examination. Specifically, the position of the near end of the image frames used to generate the breast surface map have been adjusted to account for motion detected by sensor 48. Likewise, the position of the far end of the image frames used to generate the chest wall surface map 392 have been adjusted to account for motion detected by sensor 49.

Referring again to FIG. 13, at block 396, technique 382 calculates the distance between the near ends and far ends of consecutive or sequentially attained image frames. The distance measurement can be performed between each corresponding line pixel in subsequent or neighboring line segments or between the adjacent ends of the top and bottom image lines according to alternative embodiments. Regions where the measured distances between corresponding image or line pixels exceed the predetermined spacing threshold in one or both of the surface-level and chest-wall level maps 392, 394 are marked as areas of suboptimal imaging, recorded, and displayed at blocks 398 and 400 to allow rescanning of the region.

A 2D chest wall surface map 392 and a 2D breast superficial surface map 394, obtained by projecting the 3D surface over a flat surface, are illustrated in FIGS. 15 and 16, respectively, for an exemplary ultrasound sweep. Each map 392, 394 contains a respective area 402, 404 within the breast surface contour 312 that is marked as containing suboptimal image data. Lines 406, 407 displayed in respective maps 392, 394 depict the probe positions at which image frames were acquired. Lines 406 in chest wall surface map 392 represent the far end of acquired image frames and lines 407 represent the near end of acquired image frames. Once the location of the area(s) 402, 404 containing insufficient or suboptimal image data is determined, TDMD 20 may automatically and instantly generate an alert that prompts an operator to rescan the area(s). Alternatively, alerts may be saved with the acquired image frames for later review. The dynamic mapping of the superficial and deep regions of the breast relative to different body references allows for the accurate evaluation, regardless of the tissue or patient's motion.

Other algorithms can be also used to adjust for the deformability of the breast surface at subsequent sweeps, which include normalizing the position of multiple surface line segments or reconstructed surface strips to each other or performing an elastic deformation to fit a determined or reference breast shape. For example, the cumulated image line segments positions corresponding to the surface and deep regions can be fitted to a breast model, which can be generic, generated at the beginning of the examination from the breast contour and nipple position data or any other method.

In another embodiment, the real-time linear and rotational probe speed of the top and bottom ends of the ultrasound image, relative to the nipple sensor and chest wall may be tracked together with the ultrasound frame rate during imaging in order to assess the area or volume completeness of scanning with a 2D probe within a probe sweep, respectively. The probe speed and frame rate are input in TDMD 20 to be processed with predetermined algorithms to determine the scanning quality and detect the regions for rescanning. To do so, the speed and frame rate of ultrasound probe 34 are measured and the frame rate is adjusted based on the current probe speed and probe depth. The probe depth can be set as previously described, manually or automatically. If the probe speed and frame rate are within the accepted range for the top and bottom regions of the image, the current image is labeled as an optimal image. If the speed and frame rate are outside the accepted range, the current image is labeled as a non-optimal image. Alternatively, the speed and frame rate can be calculated for each pixel in consecutive images and compared with the acceptable range. Accordingly, the region or regions with suboptimal scanning detected are represented as volumes or surface areas over the body or breast diagram to allow rescanning of the area or volume region.

Figure 18:
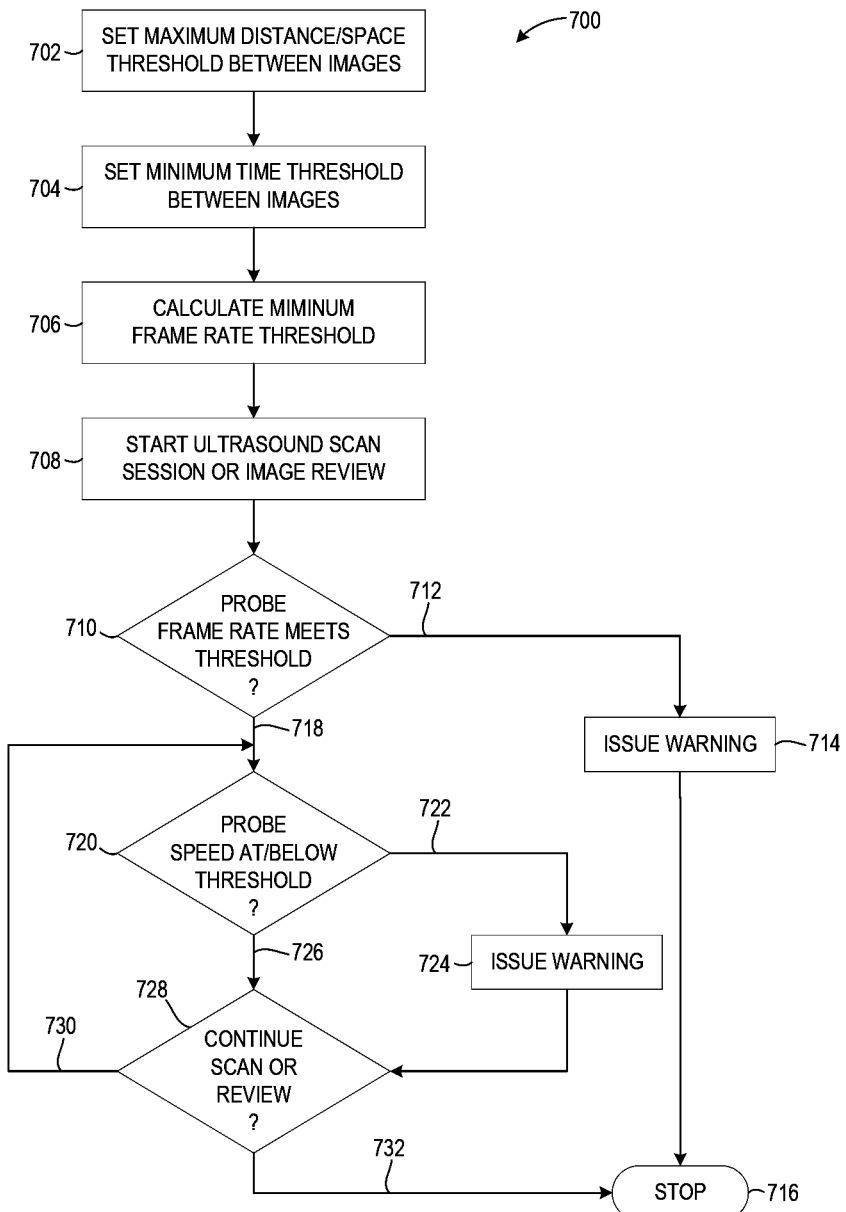
FIG. 18 illustrates a technique for tracking completeness of co-registered medical image data according to an embodiment of the invention.

FIG. 18 illustrates a technique 700 for tracking completeness of co-registered medical image data according to an embodiment of the invention. Technique 700, which can be used in combination with the above embodiments, operates to ensure that a distance is set to be detected between the near end lines or between the far end lines of sequential ultrasound images such that the images allow the inclusion of a lesion or target of the smallest size intended to be detected in at least one image. Further, the amount of time at least one image is displayed in the set distance threshold is determined to increase the chances of detection of the lesion or target within the image by a technician or other professional analyzing the acquired images for lesions/targets.

Technique 700 includes setting a maximum distance or space threshold at STEP 702. The maximum distance threshold may be set through a user input based on a distance value predetermined by the operator or other source. For a lesion/target size of no less than 3 mm to be detectable with a high rate of success, the maximum distance between sequential images may be set at a smaller distance such as 2 mm, for example. The maximum distance threshold is, therefore, set to a smaller value than the smallest detectable lesion/target desired. Other lesion/target sizes with corresponding smaller distances may be set according to embodiments of the invention. The maximum distances between successive images may be determined by detecting the distance between respective near end lines or respective far end lines of sequential images in one embodiment. This way a 3 mm lesion is included in at least one image.

At STEP 704, a minimum time threshold is set based on a minimum time that all images acquired over the space threshold are to be displayed. The minimum time threshold may be set through a user input based on a time value predetermined by the operator or other source. The minimum time threshold identifies a minimum time preferred for the display of all images within a region less than or equal to the maximum distance threshold. While the distance between sequential images is set as described above, if the images are displayed too quickly, which is all images over the maximum space threshold are displayed less than the time threshold, the ultrasound operator may miss details displayed in the image or images and fail to detect a lesion of the minimum size set above. Setting a minimum time that all images may be displayed within the maximum space threshold ensures that a target of a minimum set size is displayed long enough to be reliably detected by operators. In one embodiment, the minimum time threshold may be set to 100 ms for example. The combination of setting the maximum distance threshold and the minimum time threshold and ensuring that the thresholds are met increases the chances of a lesion/target to be detected.

From the maximum distance/space threshold set at STEP 702 and the minimum time threshold set at STEP 704, a maximum speed at which the ultrasound probe may be moved over the selected distance between each set of frames at which successive images are acquired—i.e., a "maximum probe speed threshold"—can be determined. In the above example, the maximum probe speed over each 2 mm segment would be 20 mm/s (Max Probe Speed=2 mm/100 ms). Movement of the ultrasound probe at a speed of 20 mm/s or less during image acquisition would thus be acceptable.

Parameters or settings of the ultrasound probe used in the scanning process for the imaging system include a probe frame/image rate. For each combination of desired threshold settings determined above, there is a minimum ultrasound probe image frame rate to allow the detection of images displayed in compliance with the set thresholds. At STEP 706, a minimum target probe frame rate threshold for the imaging system/ultrasound probe can be determined based on the minimum time threshold. The condition for calculating the minimum target probe frame rate can be expressed as the inverse of the minimum time for which all images acquired over the space threshold are to be displayed. The minimum target frame rate threshold may be calculated by the formula:

$$FR_{min} = \frac{1}{\text{min time threshold}} \quad \text{(EQU. 1)}$$

Using the example provided above, the minimum target frame rate ($FR_{min}$) may be calculated with the minimum display time value of 100 ms. Thus, at least one frame should be displayed over 100 ms and the minimum probe frame rate in this example should be 10 frames/second, i.e., 10 Hz.

In general, it is desirable to display the ultrasound images at frame rates that produce good motion images without interruptions, usually above 12-20 frames per second (fps). In the example provided above, at the maximum probe speed of 20 mm/s over a spacing of 2 mm between two consecutive frames (e.g., ultrasound images corresponding to a frame rate of 10 fps or 10 Hz), any frame rate below 10 Hz would increase the distance covered between two consecutive frames above 2 mm and would, therefore, not fall within the calculated minimum frame rate threshold and would not be acceptable.

Referring still to FIG. 18, prior to or after an ultrasound scanning session or image review has begun (STEP 708), technique 700 determines whether the ultrasound probe frame rate falls outside the calculated minimum frame rate threshold (STEP 710). If the ultrasound probe frame rate is not fast enough to be able to capture images within the calculated minimum frame rate threshold (STEP 712), then it is determined that tracking completeness cannot be accomplished, according to embodiments of the invention. Accordingly, the user/technician is warned (STEP 714) that the selected ultrasound probe setting is unfit for use, and technique 700 ends (STEP 716).

If the ultrasound probe frame rate is fast enough to be able to capture images within the calculated minimum frame rate threshold (STEP 718), then technique 700 proceeds such that, during the imaging session or image review, the probe speed is compared with the maximum probe speed threshold (STEP 720) to determine whether the scanning frame rate falls at/below the calculated maximum probe speed threshold. If the probe speed exceeds the maximum probe speed threshold (STEP 722), the user/operator is warned (STEP 724) and the technique 700 determines if the scan session or review can continue (STEP 728). If the probe speed falls at/below the maximum probe speed threshold (STEP 726), the scan session or review can continue (STEP 728) if it is still ongoing (STEP 730) or may end (716) if it is not (STEP 732).

Determination of the probe speed includes determining the position and orientation of the ultrasound probe (such as probe 34) as described herein. For example, operating technique 100 of FIG. 5 may be used to determine the ultrasound probe position relative to anatomical reference(s) and its orientation relative to the body anatomical planes defined in the spatial coordinate system as described in operating technique 100. The ultrasound probe position and orientation (as determined by the appropriate attached sensors) can be used to calculate the position and orientation of the images captured by the probe at the respective positions and orientations of the probe as it is moved during the scanning procedure. Various other parameters may be used to calculate the image boundaries capable of being captured by the probe to determine the near end lines and/or the far end lines of the captured images. The positions and orientations of the near or far end lines between adjacent or successive images can be used to calculate the distance between the two images to determine whether the image spacing falls within the maximum distance set at STEP 702. If either of the near end lines or the far end lines falls outside the maximum distance, the warning 724 may be sounded and/or displayed to alert the operator of the probe speed exceeding the maximum probe speed threshold.

According to embodiments of the invention, as part of the probe speed determination, different aspects or features on an ultrasound image frame may be measured or monitored. In one embodiment, the speed of the ultrasound image frame may be measured in the four corners of an/each image. If the speed in at least one corner exceeds the speed threshold, a warning or alarm is triggered (step 724), even if the speed of the other three corners is below the threshold. In another embodiment, the speed of the near and far end frame lines or end points are separately monitored and compared against the speed threshold to detect threshold violations.

The position and orientation of the ultrasound probe can also be used to determine whether the minimum time threshold is met or exceeded as part of the determination of the scanning probe speed. That is, a single image is not required to be shown for at least the minimum time as long as the collection of images within the set maximum distance are collectively shown for at least the minimum time. For example, the minimum time threshold condition may be met for showing a single image within the minimum time or may be met for showing multiple images within the maximum distance for at least the minimum time. Using the examples provided above, the minimum time threshold may be met by showing ten images for 10 ms each as long as the distance between the first and last images does not exceed the maximum distance. In this manner, the ten images displayed to the operator for a total of 100 ms satisfy the display of this region of the patient to the operator for at least the minimum time if the distance between the first and last images is less than or equal to the 2 mm maximum distance.

In one embodiment, the sequential ultrasound images can be recorded in at least one video clip or other sequence of images. For the segments of scanning where the ultrasound probe speed exceeds the allowed threshold, a video clip or sequence of the images that were recorded in a video stream can be played back to the user/technician at a lower speed to allow the display of at least one image within the set distance between sequential images for the calculated minimum amount of time or more to allow for a reliable detection.

Since the detection of small targets in ultrasound images is a complex process depending on many variables including those related to the image properties and the human physiological performance, the time needed for a segment of space to be displayed to allow the detection of small targets of a set size can vary between different ultrasound machines and operators. The determination of the specific maximum speeds over the set distances between ultrasound images to allow the reliable detection of the smallest desirable targets intended to be detected for different ultrasound machines and users for the purpose of setting the maximum distance and minimum time thresholds of technique 700 can be made using recorded test video clips obtained with the ultrasound machine and targets of known size. The images can be played at decreasing speeds until all targets are detected. Images of small artificial targets in phantoms or real small lesions from previous exams can be used. The determined maximum speed values can be used with each operator and ultrasound machine or multiple operators and ultrasound machines.

During ultrasound scanning, fatigue and loss of attention can interfere with the detection of small targets. It is also possible to have different time thresholds needed for presenting a space segment, or set distance between ultrasound images to make reliable detections, at different times. Therefore, it would be desirable to test the detection performance for small lesions during scanning the patient or during the review of images after scanning.

In one embodiment, a small target image (e.g., false target) similar in size and appearance with those intended to be detected can be implanted in the real images during scanning or reviewing of clinical images and displayed for known periods of time. The size and display time of the false targets can be varied to determine the threshold values for each operator. The shortest time needed to display a target to make a detection is recorded and can be compared with the minimum amount of time selected to display the space over the set distance between sequential images before triggering a warning. The false targets can be applied during real-time patient scanning or the routine review of clinical images after acquisition. When a false target is found, the operator is informed, and the target can be dismissed.

In the embodiment described above, if the time needed to display a target to make a reliable detection as described herein is longer than the minimum time set to display the space over the set distance corresponding to the target size between sequential images, the operator can be alerted before triggering a warning. Alternatively, the minimum time set to display the space over the set distance corresponding to the target size, between sequential images, or the maximum probe speed, can be automatically changed within a known range, to allow the detection of intended targets of minimum selected size.

The techniques described for displaying ultrasound images above can be applied for any other medical images presented in a sequential mode for interpretation. Examples of images where the techniques described above can be applied during the review of images include CT, MRI, DBT (digital breast tomosynthesis), or any other sequential images.

Figure 19:
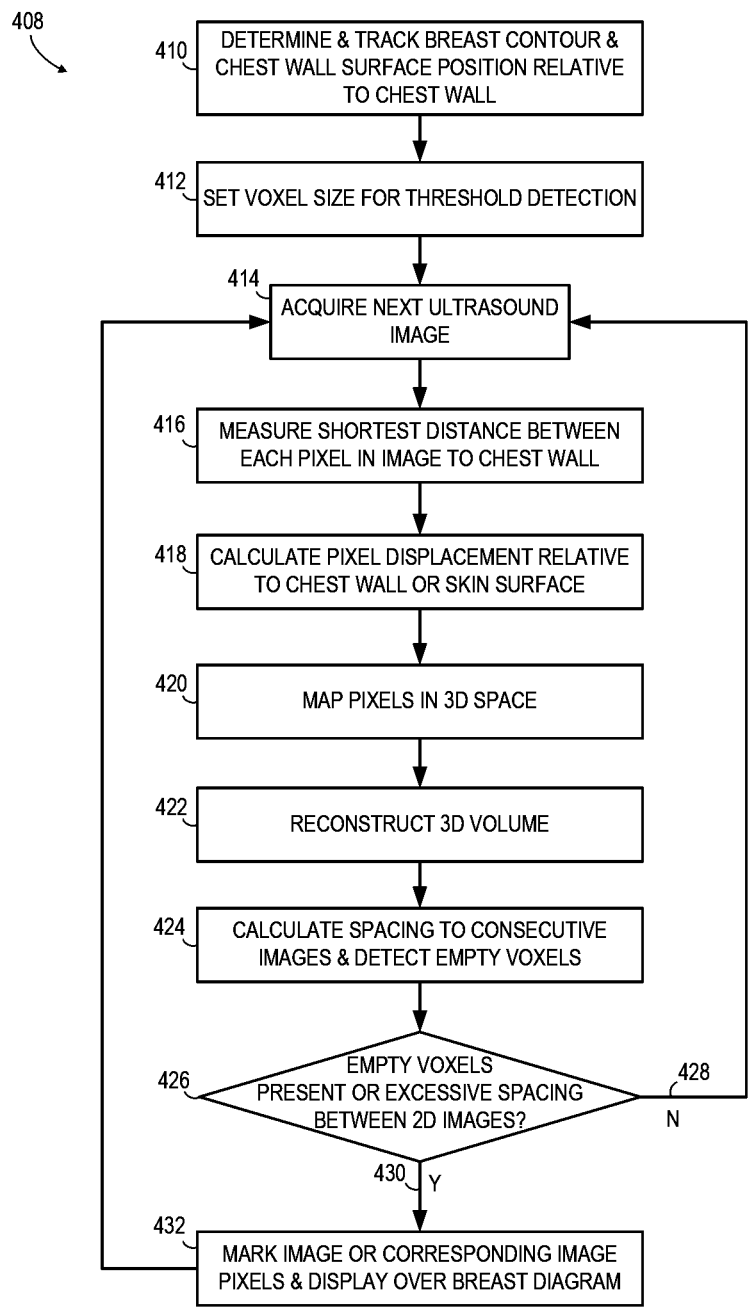
FIG. 19 is a flowchart illustrating a volumetric completeness of scanning subroutine, according to another embodiment of the invention.

FIG. 19 illustrates an alternative technique 408 for carrying out the volumetric completeness of scanning subroutine according to another embodiment of the invention. Technique 408 begins by determining and tracking the breast surface contour 312 and chest wall position relative to the chest wall at block 410. This tracking may be carried out using a body sensor 49 attached to the chest wall and one or more positions sensors coupled to the nipple C or breast skin, as described above with respect to FIG. 6. The tracked ultrasound probe 34 and corresponding image position are known in the spatial reference frame. In each ultrasound image, the superficial region tissue displacement follows the nipple C and breast skin surface, while the deeper breast tissue displacement follows the chest wall motion.

At block 412 a voxel size threshold is set that will be used to determine when the spacing between successive images is suboptimal and indicate an unacceptable amount of tissue not included in images. The voxel size threshold can be set with each examination or set to a default value according to alternative embodiments. In one non-limiting embodiment, the voxel size threshold may be set to approximately 2 cubic mm. After the voxel size threshold is set, the next ultrasound image is acquired at block 414.

Next, the distance between each pixel or group of pixels in the acquired ultrasound image and the chest wall and skin is calculated at block 416. The displacement of each pixel or group of pixels relative to the chest wall or nipple during scanning is calculated at block 418. A linear function or a more complex algorithm can be used to apply the amount of displacement to each pixel or group of pixels as a function of the distance to the chest wall and superficial skin, where the tissue closer to skin follows closer the nipple position and the tissue closer to the chest wall follows closer the chest wall position. The pixels are mapped in 3D space at block 420 and the 3D volume is reconstructed at block 422. When the pixel displacement calculations are applied to each ultrasound image in a sequence of images at block 424 the 3D coordinates of each 2D image are adjusted and a 3D image composed of voxels can be reconstructed. Subsequently, the distance between the 2D images with adjusted positional coordinates is calculated. Alternatively, in the reconstructed 3D image, empty voxels, with no image information, can be detected.

At block 426, technique 408 determines whether the distance between the 2D images or number of empty voxels exceeds the threshold. If the threshold is not exceeded 428, technique 408 returns to block 414 and acquires the next ultrasound image. If the threshold is exceeded, 430, on the other hand, the image or corresponding image pixels are marked as suboptimal at block 432. Optionally, technique 408 may additionally generate a prompt at block 432 indicating that the operator should rescan the region.

In one embodiment, the marked pixels or voxels corresponding to the 2D images with excessive spacing or empty voxels are displayed in the breast diagram, as illustrated in FIGS. 15 and 16. Alternatively, or in addition thereto, the ultrasound image position corresponding to the empty voxels may be displayed in the breast diagram 308, as illustrated in FIG. 17. While FIGS. 15, 16, 17 depict the regions with empty voxels as projections over a 2D breast diagram, it is contemplated that the empty voxels may similarity illustrated over a 3D breast diagram, similar to that of FIG. 6.

Referring again to FIG. 12, following the volumetric completeness subroutine 380 technique 368 determines whether the scan is complete at block 434. In one embodiment, technique 368 does so by detecting whether the head 35 of ultrasound probe 34 is in contact with the skin. If the head 35 of ultrasound probe 34 remains in contact with the skin, the scan sweep is not complete 436 and technique 368 continues acquiring image data at block 370. If the probe head 35 is not in contact with the skin, the scan sweep is determined to be complete 438. In an alternative embodiment, the start and end frames for a given sweep may be manually activated by the operator.

Figure 22:
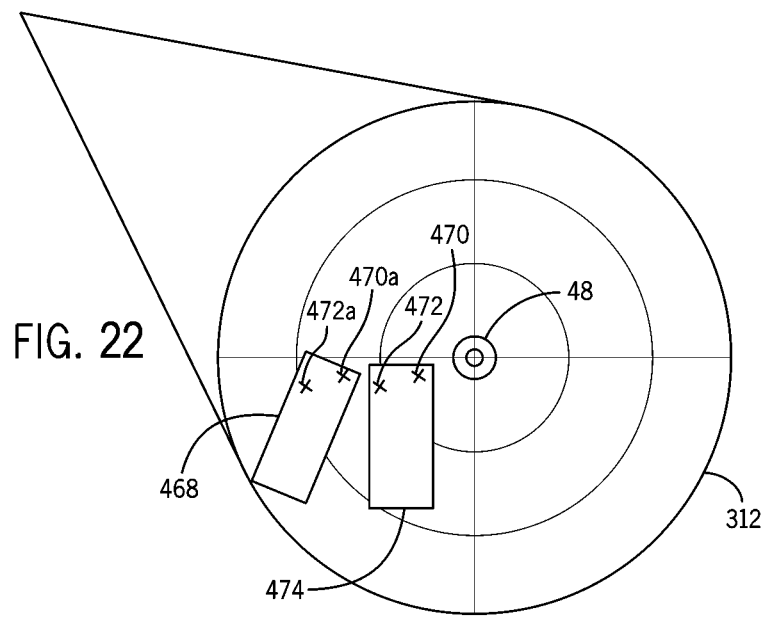
FIG. 22 illustrates a completeness map generated from two surface maps with common surface markers before realignment.
Figure 23:
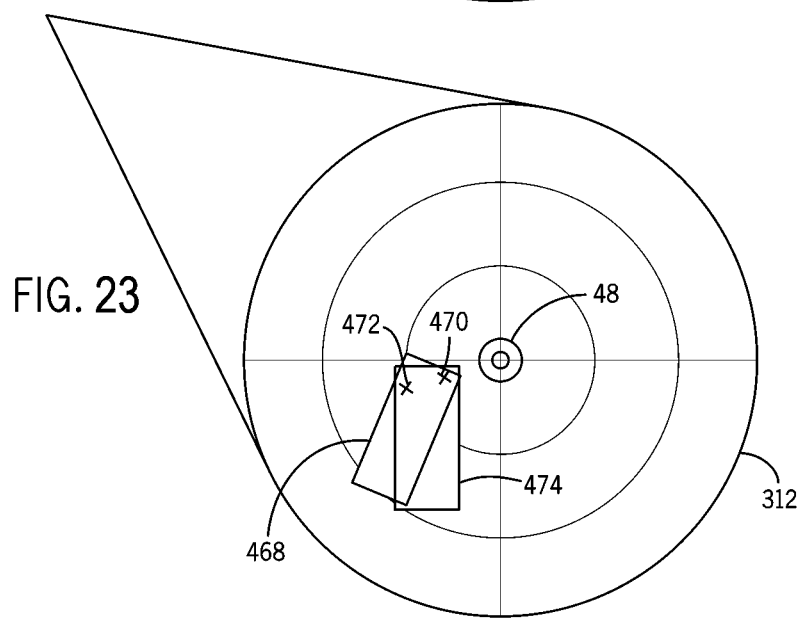
FIG. 23 illustrates a completeness map generated from the two exemplary surface maps of FIG. 21 after realignment.
Figure 24:
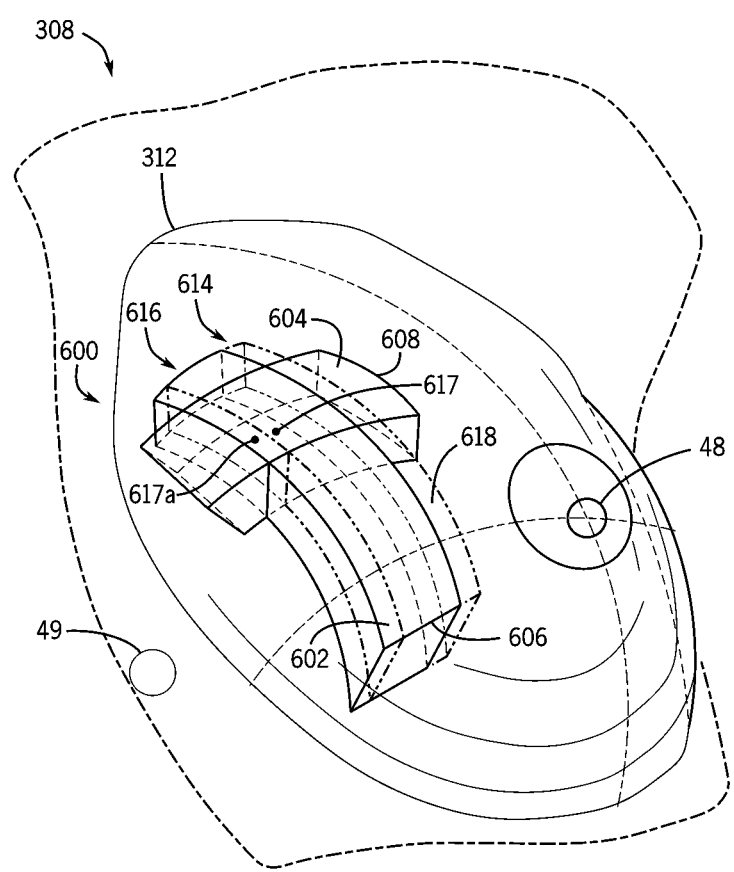
FIG. 24 shows a completeness of scanning map with the 3D breast diagram and alignment of segments with common points.

Once the scan is complete, technique 368 transitions to block 440 during which a completeness map is generated. An exemplary completeness map 600 is shown in FIG. 24 as an overlay on breast diagram 308 and includes surface area segments 602, 604 generated from two scan sweeps of the ultrasound probe 34. Surface area segments 602, 604 may be generated by connecting the sequential line segments in a respective sweep or row into band-like area segments 602, 604 that are generated and displayed over the breast diagram 308, as illustrated in FIG. 24. Because each line segment representing the near end of the image frame and corresponding to the probe head 35 position and orientation can be dynamically referenced by TDMD 20 to the nipple point position and to the patient's body planes position and orientation, the location of area segments 602, 604 may be co-registered and displayed over the registered body or 3D breast diagram 308 and breast surface contour 312. Area segments may displayed in a 2D breast diagram in a similar manner, as shown in FIGS. 22 and 23. Completeness map 600 may be used by an operator to identify the breast surface areas not covered by ultrasound probe 34 based on areas of the breast surface contour not covered by the surface area segments 602, 604. As shown, multiple surface area segments 602, 604 generated from multiple sweeps can be displayed together to assess the completeness of scanning of the skin surface area inside breast surface contour 312. To determine the completeness of scanning for the area or volume within the breast surface contour 312, the position and orientation of every ultrasound image frame and corresponding ultrasound probe 34 can be measured in real time, displayed and recorded by TDMD 20.

In an alternative embodiment, the cumulated positions of ultrasound probe 34 may be illustrated by displaying the position each image over a breast diagram. FIG. 14 provides an exemplary depiction of the relative position of ultrasound images acquired in two sweeps 112, 114 over a breast diagram 308. Such a cumulated display of the acquired images may be shown during and/or after an examination, to allow an operator or interpreter to assess the total area or volume covered by the saved images. When displayed in real time, the cumulative area of the transducer positions where the ultrasound images of breast tissue were generated allows for a quick evaluation of ultrasound examination completeness and demonstrate the region evaluated by the operator.

Regardless of the method used to detect the images containing the tissue information, the cumulated map of probe positions and area segments can be displayed over the body diagram. The real-time display of the cumulated covered breast area during an examination can guide the ultrasound user to scan the regions not yet covered and complete the examination without missing any breast skin surface. For a completed examination submitted for interpretation at a later time, the cumulated covered breast surface area can be displayed over the body or breast diagram and contour to assess the completeness of coverage. Overlapping area segments can be represented with a different color or pattern and the gaps which represent breast skin areas where no images were obtained can have different color or pattern on the display and/or in the saved images. The missed areas can be detected by the operator or automatically detected by TDMD 20 using pattern detection or other algorithms with area maps generated by TDMD 20. When automatically detected, TDMD 20 may be configured to output a visual and/or audible alert to notify the operator of missed area or volume regions.

Each line segment corresponding to the probe head position and orientation can be dynamically referenced by TDMD 20 to the nipple point position and sensor and to the patient's body planes orientation and displayed over the body or breast diagram and breast surface contour. During subsequent sweeps over the breast skin, the 3D position of the skin surface relative to the anatomical reference points and planes can be different due to the breast inherent deformability and therefore gaps can be inadvertently recorded between adjacent or overlapping area segments. To mitigate this limitation, the line segments in a sweep or a reconstructed area map can be projected over a plane or surface like the surface generated by the breast surface contour or a plane perpendicular to the scanning plane or average scan plane coordinates.

After a completeness map 600 is generated, technique 368 enters an optional segment realign subroutine 442 (shown in phantom). Due to the breast's deformability and motion relative to the chest wall and body, the position of each 2D frame in an ultrasound sweep or of multiple sweeps with the corresponding covered area segment or volume segment relative to the chest wall, nipple or other body reference may be slightly shifted from the position it would be expected with a non-deformable structure as a result of the tissue deformation resulting from the pressure imposed by the head 35 of the ultrasound probe 34 on the skin surface during the scanning session. Furthermore, within the same volume of scanning, there may be structures with different deformability and elastic properties, like pliable fat lobules or cysts versus firm structures like a fibro adenoma or malignant tumor which can move in a more deformable glandular or fatty surrounding environment, which further complicate the alignment of serial images or segments of area or volume in composite maps to assess the completeness of scanning. To mitigate the described limitations, the segment realign subroutine 442 may be used identify common points in the multiple scanned segments or sweeps and use them to assemble a more accurate mapping of completeness of scanning.

Figure 20:
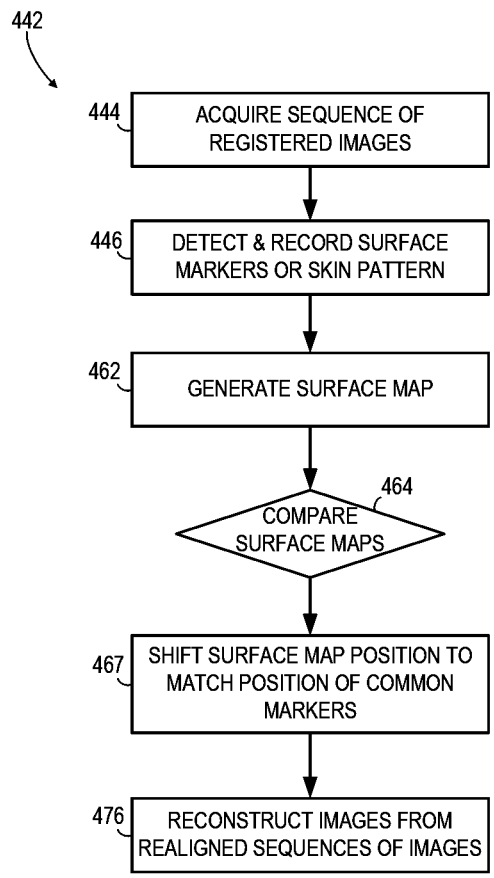
FIG. 20 is a flowchart illustrating a subroutine for realigning image segments, according to an embodiment of the invention.
Figure 21:
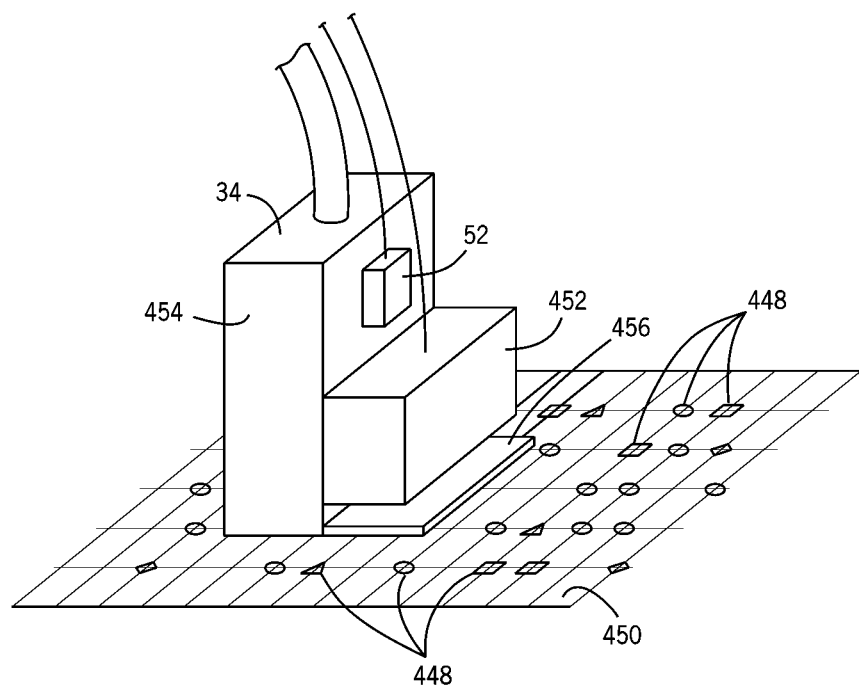
FIG. 21 is a schematic illustration of an ultrasound probe having a camera attached thereto, according to an embodiment of the invention.

Segment realign subroutine 442 is described in additional detail with respect to FIGS. 20 and 21. Segment realign subroutine 442 begins at block 444 by acquiring a sequence of ultrasound images. The acquired ultrasound images are registered with the nipple position, body orientation, in the manner described above with respect to FIG. 6. During image acquisition, skin surface data is detected and recorded at block 446. In one embodiment, the skin surface data is acquired using an array of surface markers 448 that are fixed relative to the breast skin 450 of the patient A during imaging, as shown in FIG. 21. The array of surface markers 448 is applied in a pattern that would enable to identify them when a repeat surface image of same region is taken. The array of surface markers 448 is detected using one or more optical cameras 452 coupled to the housing 454 of ultrasound probe 34. These optical cameras 452 acquire surface images of the skin 450 while scanning. These optical surface images are calibrated to the position of ultrasound probe 34, as described in detail below, and are then used to map the skin surface. Transparent plate 456 is attached to ultrasound probe 34 and positioned such to be substantially co-planar with the outward facing surface 458 of the probe head 460. Transparent plate 456 aids in flattening the skin during the scan.

In an alternative embodiment, the array of surface markers 448 are ultrasound reflectors embedded in an ultrasound standoff transparent layer over the breast. In this embodiment, housing 454 of ultrasound probe 34 is fitted with optical detectors/emitters (not shown), which detect and map a network of surface optical reflectors.

In yet another embodiment, optical cameras 452 are able to analyze the skin surface pattern and identify unique patterns on the skin in the absence of applied markers. According to various embodiments, the unique skin patterns may be determined based on the position of freckles, scars, or natural marks on the skin, or based on the skin texture. In such an embodiment, optical cameras 452 operate with visible light, infrared light or other wavelength and obtain surface images.

In the above-described embodiments, the images captured by the optical cameras 452 (or the image data captured by the optical detectors/emitters on ultrasound probe 34) are calibrated to ultrasound probe 34 with the position sensor 52. Therefore, the position of each image and detected markers or skin patterns in the optical surface images obtained with the camera 452 is known relative to ultrasound probe 34, and relative to the anatomical landmarks like nipple and body orientation planes. The cumulated surface images obtained with the camera 452 in a sequence of ultrasound images, or sweep, overlaps with the surface ultrasound probe positions. As a result, the acquired ultrasound images and optical surface images may be used at block 462 to generate a surface map of the positions of the head of ultrasound probe 34 and the corresponding surface markers or detected skin pattern.

During block 464, the surface area segments with the co-registered ultrasound images and optical surface images obtained as above are compared and the common patterns are fitted together to generate a larger region with composite aligned areas. More specifically, the generated surface maps are compared with other surface maps acquired during the same examination to determine whether similar marks or skin patterns are detected between the maps. If similar markers or a similar skin pattern are detected between two surface maps, the position of one of the surface maps is shifted so that the position of the common surface markers or skin pattern in the two surface maps match at block 467. Once the surface map positions have been shifted, the positions of the ultrasound images associated with the surface probe positions may be realigned as well at block 476, individually for each ultrasound image or for an entire volume when the volumetric images are reconstructed before the realignment. The realigned frames or 2D ultrasound images are then reconstructed in 3D images. The image shifting can be performed using algorithms which would account for less displacement closer to the chest wall.

This surface map shifting process is schematically illustrated in FIGS. 22 and 23. Referring first to FIG. 22, two surface markers detected using optical camera 452, marker 470 and marker 472, are associated with surface map 468 generated from ultrasound image data acquired using ultrasound probe 34. Likewise, surface markers 470a and 472a, which were detected using optical camera 452, are associated with surface map 474 generated from ultrasound image data acquired using ultrasound probe 34. If segment realign subroutine 442 determines that the markers 470, 472 correspond to markers 470a and 472a, TDMD 20 will shift surface map 474 so that the marker 470 is aligned with marker 470a and marker 472 is aligned with marker 472a, as shown in FIG. 23. To do so, TDMD 20 realigns the optical images acquired using optical camera 452 so that the position of the common markers 470/470a and 472/472a match. Since the optical images are co-registered with the ultrasound images, shifting the optical images will also realign the corresponding ultrasound images to account for any misalignments in the ultrasound images that occurred due to deformation caused by the ultrasound transducer or other factors.

Additionally, to align the volumes underneath the area segments corresponding to each surface map, common points or landmarks 617, 617a can be manually or automatically selected and matched in multiple volume segments 606, 608 to improve the alignment of overlapping volume segments, as illustrated in FIG. 24. The common points 617, 617a may represent small structures like cysts, calcifications, vessels crossings, fiducial markers which can be identified and matched.

Referring again to FIG. 12 and continuing with the description of technique 368, the acquired area or volume segments are fit and displayed in the breast diagram at block 478. Next, segments with no image data (e.g., empty voxels) or sub-optimal scanning are detected and displayed at block 480.

When a second scanning segment or band is obtained in a parallel direction with the first segment, an area or volume of overlapping may be needed to ensure the entire breast volume was imaged. An algorithm can be used to determine the overlapping of segments, and an alarm can be triggered when insufficient overlapping is present.

Optionally, an alert may be generated at block 482 (shown in phantom) when segments with no or sub-optimal scanning are present. Technique 368 next determines if the scanning session is complete at block 484. If so 486, the images and completeness maps are saved at block 488. If the scanning session is not complete 490, technique 368 returns to block 370 and continues acquiring image data.

FIG. 24 illustrates the effects of a shifting process when applied to two imaged volumes 606, 608 based on the position of a common marker 617/617a located within the breast volume. After imaging, volume 606 is initially illustrated at a first position 614 on the breast diagram 308 and is shifted downwards and to the left to arrive at a second position 616. The portion 618 of the original volume 606 that is no longer included at the second position 616 may be depicted on the breast diagram 308 as a volume of tissue that was missed in the scan sequence, to allow the operator to rescan the region and acquire the missing image data.

The completeness of scanning technique 368 is automated and warnings can be set to alert the operator and point to the volumes of tissue not included in the obtained set of images.

Figure 25:
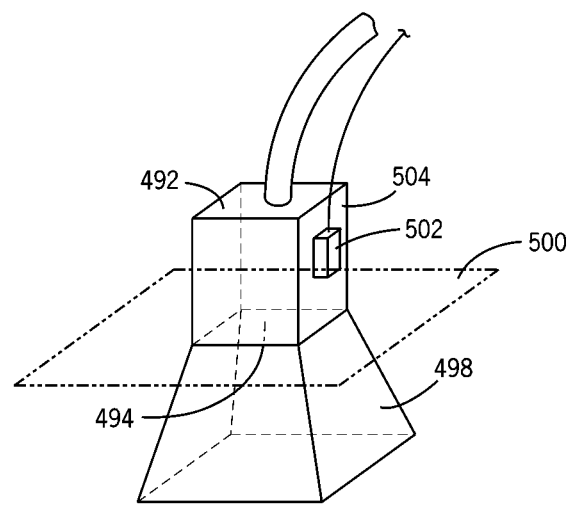
FIG. 25 is a schematic illustration of a 3D ultrasound probe with the field of view and attached position sensor.

While embodiments of the invention are described above with respect to a 2D ultrasound probe used for the breast or other body parts scanning, alternative embodiments of the invention may employ a 3D ultrasound probe for tissue scanning, such as 3D ultrasound probe 492 schematically illustrated in FIG. 25. 3D ultrasound probe 492 has a broader scan head 494 or scan surface than a 2D ultrasound probe and generates images of the underlying tissue in the shape of a volume 496 of known shape and size that corresponds to the field of view 498 of the 3D ultrasound probe 492, instead of the 2D planar images generated by a traditional 2D ultrasound probe. 3D ultrasound probe 492 uses an array of crystals which generate the ultrasound beams which can be mechanically or electronically steered in one or more directions to cover the volume under the probe and create the 3D images. To obtain 3D images with good quality and resolution, the 3D ultrasound probe is held still for a few seconds during the image acquisition. The 3D images offer several advantages when compared to the 2D ultrasound probes, including the ability to reconstruct the underlying volume more accurately than the reconstruction of 2D images obtained with 2D ultrasound probes and display the coronal, or C plane 500 in the volumetric images, which is parallel with the probe head surface. It is demonstrated that adding the C plane 500 to the evaluation of breast lesions, the sensitivity and specificity of the ultrasound examination is enhanced. Although it is possible to reconstruct 3D images from the 2D sequential images acquired using a 2D ultrasound probe, the motion of tissue underlying the 2D ultrasound probe during sweeping over the skin prevents the reconstruction of accurate 3D images, even with high frequency images acquisition.

The 3D probe calibration with the 3D image is similar with the calibration of the 2D ultrasound probes, and the volume and shape underneath the 3D ultrasound probe 492 is positionally calibrated with one or more position sensors 502 attached to the probe housing 504. When each plane or surface that borders the 3D field of view 498 under the 3D ultrasound probe head 494 is calibrated, similar to calibrating a 2D image with the 2D ultrasound probes, the 3D field of view 498 is calibrated with 3D ultrasound probe 492. Any known method to calibrate the 3D image of a 3D ultrasound probe 492 may be used. Once 3D ultrasound probe 492 is calibrated, every voxel in the ultrasound images can be tracked and referenced to the positional sensors and other positional references, as described above with TDMD for the 2D probes. When the 3D ultrasound probe 492 is held still during a 3D image acquisition, the image resolution and uniformity is maintained in the entire acquired volume in all directions, as allowed by the probe design.

To assess the completeness of scanning with the 3D ultrasound probe 492, the spacing measurements between 2D images is no longer needed to assess the volumetric completion of scanning, when the 3D ultrasound probe 492 is held still during the entire 3D image acquisition step, without tissue motion relative to the nipple or chest wall during the same 3D image acquisition. The 3D image quality is maintained throughout the entire scanned volume under the 3D probe field of view 498. However, one field of view covers a limited volume, as allowed by the design of probe 492. To verify the acquisition of larger volumes of tissue with multiple 3D samplings, it would therefore be desirable to map and stitch together the 3D coordinates of each volume portion acquired with the handheld 3D probe or other type of 3D probes, like the automated large field of view systems. This task can be obtained in a similar way as described above for 2D ultrasound probe 34. In one embodiment, after the setting and registration of the nipple sensor 48, body or sternum sensor 49 and the breast surface and breast surface contour 312, the calibrated 3D ultrasound probe 492 with the position tracking sensor(s) 502 and corresponding spatial frame or field of view 498 can be calculated and displayed in real time over the oriented breast and anatomical references diagram. The position of each volume portion and probe head surface, for each 3D image set is displayed over the 3D breast diagram, and can be cumulated to display multiple 3D volumes of individual 3D acquisition portions, covering the breast volume and surface.

The surface or volume regions, not included in the 3D volume portions are identified, displayed and stored, which can guide the ultrasound operator to apply the 3D probe over the entire surface of the breast and include the entire breast volume, in a similar manner as illustrated in FIG. 24 for a 2D ultrasound probe (albeit with 3D image sets).

The surface and volume registration and alignment between multiple volumetric 3D images can be performed using the same methods described for area or volume segments obtained with 2D ultrasound probe 34. Since the 3D ultrasound probe 492 is not usually moved during the acquisition of a volume image, there is no need to track the probe speed and match the frame rate automatically. However, the motion of the 3D probe during a 3D image acquisition can lead to suboptimal images, therefore, the handheld 3D probe motion during a 3D probe acquisition can be detected and prompt to rescan the underlying volume without probe motion. The surface and volumetric realignment can be performed with the use of common surface marker detection when using optical or infrared camera(s) attached to the 3D probe, or volumetric common points, as described for the 2D ultrasound probes. The probe skin contact can be determined using the same methods described above for 2D ultrasound probe 34.

The depth of 3D ultrasound probe 492 frame or field of view 498 is known and when the chest wall is mapped as described above, the completeness of the scan and ultrasound optimal parameters setting can be performed as described above for 2D ultrasound probe 34.

A technical contribution for the disclosed method and apparatus is that it provides for a computer implemented technique for determining the completeness of co-registered medical image data scanning. The completeness of medical image scanning relies on measuring the amount of space presented to an interpreter in sequential images during a set period of time, determined to be needed to make a detection, during or after scanning a patient. When the amount of space exceeds a set threshold, the interpreter is informed. Measuring the amount of space presented to an interpreter in sequential images during a set period of time, determined to be needed to make a detection, can be performed during the display of sequential medical images, included but not limited to ultrasound, mammography with tomosynthesis, MRI, CT scans or any other images presented in a sequential mode.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to one embodiment of the invention, an ultrasound image tracking completeness system includes an ultrasound imaging probe configured to acquire images during an examination, the images calibrated to the ultrasound imaging probe. The ultrasound image tracking completeness system also includes an imaging probe sensor coupled to the ultrasound imaging probe, the imaging probe sensor comprising a magnetic sensor configured to track a position and an orientation of the ultrasound imaging probe. The ultrasound image tracking completeness system further includes a display included on or separate from the ultrasound imaging probe and configured to display the images acquired by the ultrasound imaging probe and a processor programmed to calculate a probe speed threshold at which the ultrasound imaging probe may be moved while acquiring images during the examination, track the position and orientation of the ultrasound imaging probe during the examination by monitoring the imaging probe sensor, determine a movement speed of the ultrasound imaging probe during the examination, and if the movement speed of the ultrasound imaging probe exceeds the probe speed threshold, issue a warning to an operator.

In accordance with another embodiment of the invention, a method for tracking image completeness includes identifying an orientation and a position of an ultrasound imaging probe of an ultrasound imaging system relative to the ultrasound imaging system during an examination and acquiring image data from a patient using the ultrasound imaging probe during the examination, the image data calibrated to the ultrasound imaging probe. The method also includes tracking a position and an orientation of the ultrasound imaging probe during the examination using a magnetic sensor coupled to the ultrasound imaging probe, reconstructing a first image of the patient from the image data that comprises a first plurality of pixels, and reconstructing a second image of the patient from the image data that comprises a second plurality of pixels. The method further includes calculating a probe speed of the ultrasound imaging probe based on the tracked position and orientation of the ultrasound imaging probe, determining whether the probe speed meets a probe speed threshold, displaying, on a display, at least one of the first and second images, and generating a warning to an operator if the probe speed fails to meet the probe speed threshold.

In accordance with yet another embodiment of the invention, a tracking completeness system includes an ultrasound imaging probe configured to acquire a plurality of images during an examination, the plurality of images calibrated to the ultrasound imaging probe. The tracking completeness system also includes an imaging probe sensor coupled to the ultrasound imaging probe, the imaging probe sensor comprising a magnetic sensor configured to track a position and an orientation of the ultrasound imaging probe. The tracking completeness system further includes a display configured to display the plurality of images acquired by the ultrasound imaging probe and a processor programmed to set a maximum distance threshold, set a minimum time threshold, calculate a probe speed threshold based on the maximum distance threshold and the minimum time threshold, track the position and orientation of the ultrasound imaging probe during the examination by monitoring the imaging probe sensor, calculate a movement speed of the ultrasound imaging probe from the plurality of images acquired by the ultrasound imaging probe, determine whether the movement speed of the ultrasound imaging probe exceeds the probe speed threshold, and if the movement speed of the ultrasound imaging probe exceeds the probe speed threshold, provide a warning to an operator that the movement speed of the ultrasound imaging probe exceeds the probe speed threshold.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A tracking completeness system comprising:
   an ultrasound imaging probe configured to acquire a plurality of images during an examination, the plurality of images calibrated to the ultrasound imaging probe;
   an imaging probe sensor coupled to the ultrasound imaging probe, the imaging probe sensor comprising a magnetic sensor configured to track a position and an orientation of the ultrasound imaging probe;
   a display configured to display the plurality of images acquired by the ultrasound imaging probe; and
   a processor programmed to:
      set a maximum distance threshold, wherein the maximum distance threshold is set to a smaller value than the smallest detectable target desired;
      set a minimum time threshold, wherein the minimum time threshold identifies a minimum time to display all of a set of images within a region that is less than or equal to the maximum distance threshold;
      calculate a maximum probe speed threshold based on the maximum distance threshold and the minimum time threshold, wherein the maximum probe speed threshold identifies a maximum speed at which the ultrasound probe may be moved;
      track the position and orientation of the ultrasound imaging probe during the examination by monitoring the imaging probe sensor;
      calculate a movement speed of the ultrasound imaging probe from the plurality of images acquired by the ultrasound imaging probe;
      determine whether the movement speed of the ultrasound imaging probe exceeds the probe speed threshold; and
      if the movement speed of the ultrasound imaging probe exceeds the maximum probe speed threshold, provide a warning to an operator that the movement speed of the ultrasound imaging probe exceeds the probe speed threshold.

2. The tracking completeness system of claim 1, wherein the processor, in being programmed to calculate the movement speed of the ultrasound imaging probe, is programmed to:
   calculate positions of the plurality of images; and
   calculate the movement speed of the ultrasound imaging probe based on the positions of the plurality of images and based on a time of display of the plurality of images.

3. The tracking completeness system of claim 2, wherein the processor, in being programmed to calculate the movement speed of the ultrasound imaging probe, is programmed to:
   measure an ultrasound image frame speed in four corners of respective images of the plurality of images; and
   provide the warning to the operator if the ultrasound image frame speed exceeds a frame speed threshold in at least one corner of the four corners.

4. The tracking completeness system of claim 2, wherein the processor, in being programmed to calculate the movement speed of the ultrasound imaging probe, is programmed to:
   measure an ultrasound image frame speed at near and far end frame lines of respective images of the plurality of images; and
   provide the warning to the operator if the ultrasound image frame speed exceeds a frame speed threshold at one or both of the near and far end frame lines.

5. The tracking completeness system of claim 1, wherein the processor, in being programmed to determine whether the movement speed of the ultrasound imaging probe exceeds the probe speed threshold, is programmed to determine whether a distance between any two images of the plurality of images exceeds the maximum distance threshold.

6. The tracking completeness system of claim 1, wherein the processor is programmed to determine a minimum probe frame rate threshold above which images are to be acquired during examination so as to include at least one image within the maximum distance threshold, the minimum probe frame rate threshold being an inverse of the minimum time threshold.

7. The tracking completeness system of claim 6, wherein the processor is further programmed to:
   determine a probe frame rate of the ultrasound imaging probe;
   determine whether the probe frame rate of the ultrasound imaging probe meets the minimum frame rate threshold; and
   if the probe frame rate fails to meet the minimum frame rate threshold, display a warning on the display to the operator.

* * * * *